(12) United States Patent
Krebs et al.

(10) Patent No.: US 11,944,392 B2
(45) Date of Patent: *Apr. 2, 2024

(54) SYSTEMS AND METHODS FOR GUIDING A REVISION PROCEDURE

(71) Applicant: MAKO Surgical Corp., Weston, FL (US)

(72) Inventors: Viktor Krebs, Weston, FL (US); Hyosig Kang, Weston, FL (US); Snehal Kasodekar, Weston, FL (US); Matt Harrow, Weston, FL (US); Jienan Ding, Weston, FL (US); Ta-Cheng Chang, Weston, FL (US); Min Wu, Weston, FL (US); Jean Gonzalez, Weston, FL (US); Peter Ebbitt, Weston, FL (US)

(73) Assignee: MAKO Surgical Corp., Weston, FL (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/387,643

(22) Filed: Jul. 28, 2021

(65) Prior Publication Data

US 2021/0353367 A1    Nov. 18, 2021

Related U.S. Application Data

(63) Continuation of application No. 17/134,774, filed on Dec. 28, 2020, which is a continuation of application
(Continued)

(51) Int. Cl.
*A61B 34/20* (2016.01)
*A61B 5/055* (2006.01)
(Continued)

(52) U.S. Cl.
CPC ............. *A61B 34/20* (2016.02); *A61B 5/055* (2013.01); *A61B 6/032* (2013.01); *A61B 8/0875* (2013.01);
(Continued)

(58) Field of Classification Search
CPC ......... A61B 34/20; A61B 34/30; A61B 17/17; A61B 17/1703; A61B 17/15; A61B 5/055;
(Continued)

(56) References Cited

U.S. PATENT DOCUMENTS 5,769,092 A    6/1998    Williamson, Jr.
5,961,523 A   10/1999    Masini
(Continued)

FOREIGN PATENT DOCUMENTS

CN    102933163    2/2013
CN    104720877    6/2015
(Continued)

OTHER PUBLICATIONS

U.S. Appl. No. 15/436,460, filed Feb. 17, 2017, Mako Surgical Corp.
(Continued)

*Primary Examiner* — Christopher J Beccia
(74) *Attorney, Agent, or Firm* — FOLEY & LARDNER LLP

(57) ABSTRACT

A method for intraoperative planning and facilitating a revision arthroplasty procedure includes displaying a virtual model of a bone, capturing positions of a tracked probe as the tracked probe contacts points at a perimeter of a primary implant component coupled to the bone, generating a virtual representation of an interface between the primary implant component and the virtual model of the bone using the positions of the tracked probe, planning a bone resection
(Continued)

using the virtual representation of the interface, and guiding execution of the bone resection.

20 Claims, 9 Drawing Sheets

Related U.S. Application Data

No. 16/923,192, filed on Jul. 8, 2020, now Pat. No. 11,484,368, which is a continuation of application No. 15/649,416, filed on Jul. 13, 2017, now Pat. No. 10,716,630.

(60) Provisional application No. 62/363,037, filed on Jul. 15, 2016.

(51) Int. Cl.
| | |
|---|---|
| *A61B 6/03* | (2006.01) |
| *A61B 8/08* | (2006.01) |
| *A61B 17/15* | (2006.01) |
| *A61B 17/17* | (2006.01) |
| *A61B 34/30* | (2016.01) |
| *A61B 90/00* | (2016.01) |
| *A61B 34/10* | (2016.01) |

(52) U.S. Cl.
CPC .......... *A61B 17/15* (2013.01); *A61B 17/1703* (2013.01); *A61B 34/30* (2016.02); *A61B 90/361* (2016.02); *A61B 2034/102* (2016.02); *A61B 2034/105* (2016.02); *A61B 2034/2055* (2016.02); *A61B 2034/2065* (2016.02); *A61B 90/37* (2016.02); *A61B 2090/3983* (2016.02)

(58) Field of Classification Search
CPC .. A61B 5/05; A61B 6/032; A61B 6/03; A61B 8/0875
See application file for complete search history.

(56) References Cited

U.S. PATENT DOCUMENTS

| | | | |
|---|---|---|---|
| 6,002,859 A | 12/1999 | Digioia, III et al. |
| 6,685,711 B2 | 2/2004 | Axelson et al. |
| 6,917,827 B2 | 7/2005 | Kienzle |
| 7,392,076 B2 | 6/2008 | De La Barrera |
| 7,477,926 B2 | 1/2009 | McCombs |
| 7,594,933 B2 | 9/2009 | Kammerzell et al. |
| 7,780,681 B2 | 8/2010 | Sarin et al. |
| 7,835,778 B2 | 11/2010 | Foley et al. |
| 7,927,338 B2 | 4/2011 | Laffargue et al. |
| 7,932,825 B2 | 4/2011 | Berger |
| 8,010,180 B2 | 8/2011 | Quaid et al. |
| 8,249,318 B2 | 8/2012 | Schmitt et al. |
| 8,337,426 B2 | 12/2012 | Nycz |
| 8,337,508 B2 | 12/2012 | Lavallee et al. |
| 8,382,765 B2 | 2/2013 | Axelson et al. |
| 8,400,312 B2 | 3/2013 | Hotokebuchi et al. |
| 8,449,551 B2 | 5/2013 | Amiot et al. |
| 8,454,609 B2 | 6/2013 | Petit et al. |
| 8,498,744 B2 | 7/2013 | Odermatt et al. |
| 8,506,645 B2 | 8/2013 | Blaylock et al. |
| 8,512,346 B2 | 8/2013 | Couture |
| 8,556,074 B2 | 10/2013 | Turner et al. |
| 8,603,093 B2 | 12/2013 | Hakki |
| 8,709,016 B2 | 4/2014 | Park et al. |
| 8,731,253 B2 | 5/2014 | Dardenne et al. |
| 8,774,900 B2 | 7/2014 | Buly et al. |
| 8,861,818 B2 | 10/2014 | Ito et al. |
| 8,891,847 B2 | 11/2014 | Helm et al. |
| 8,979,859 B2 | 3/2015 | Leparmentier et al. |
| 8,998,910 B2 | 4/2015 | Borja et al. |
| 9,017,335 B2 | 4/2015 | Stiehl |
| 9,031,284 B2 | 5/2015 | Spath |
| 9,044,173 B2 | 6/2015 | Crouch |
| 9,060,794 B2 | 6/2015 | Kang et al. |
| 9,125,669 B2 | 9/2015 | Ranawat et al. |
| 9,125,702 B2 | 9/2015 | Witt |
| 9,179,983 B2 | 11/2015 | Heavener et al. |
| 9,220,510 B2 | 12/2015 | Cheal et al. |
| 9,247,998 B2 | 2/2016 | Hladio et al. |
| 9,345,552 B2 | 5/2016 | Janik et al. |
| 9,399,298 B2 | 7/2016 | Kang |
| 9,402,726 B2 | 8/2016 | Linderman et al. |
| 9,408,617 B2 | 8/2016 | Ranawat et al. |
| 9,427,320 B2 | 8/2016 | Meridew |
| 9,668,867 B2 | 6/2017 | Kelley |
| 9,675,273 B2 | 6/2017 | Gluncic |
| 9,713,539 B2 | 7/2017 | Haimerl et al. |
| 9,763,747 B2 | 9/2017 | Kang et al. |
| 9,775,681 B2 | 10/2017 | Quaid et al. |
| 9,808,261 B2 | 11/2017 | Gelaude et al. |
| 9,877,793 B2 | 1/2018 | Bonutti |
| 9,949,797 B2 | 4/2018 | Meridew et al. |
| 9,955,983 B2 | 5/2018 | Aghazadeh |
| 9,955,984 B2 | 5/2018 | Winslow et al. |
| 10,010,377 B2 | 7/2018 | Iorgulescu et al. |
| 10,070,903 B2 | 9/2018 | Blau |
| 10,085,804 B2 | 10/2018 | Nortman et al. |
| 10,194,991 B2 | 2/2019 | Bonny et al. |
| 10,206,688 B2 | 2/2019 | Park et al. |
| 10,231,739 B1 | 3/2019 | Bonutti |
| 10,231,790 B2 | 3/2019 | Quaid et al. |
| 10,265,127 B2 | 4/2019 | Jaramaz et al. |
| 10,265,193 B2 | 4/2019 | Sherman et al. |
| 10,271,886 B2 | 4/2019 | Abiven |
| 10,285,683 B2 | 5/2019 | Plaskos et al. |
| 10,314,666 B2 | 6/2019 | Aghazadeh |
| 10,321,961 B2 | 6/2019 | McCarthy et al. |
| 10,327,904 B2 | 6/2019 | Otto et al. |
| 10,363,149 B2 | 7/2019 | Van Der Walt et al. |
| 10,390,966 B2 | 8/2019 | Clary et al. |
| 10,398,514 B2 | 9/2019 | Ryan et al. |
| 10,405,910 B2 | 9/2019 | Netravali et al. |
| 10,456,205 B2 | 10/2019 | Meridew et al. |
| 10,463,415 B2 | 11/2019 | Walter et al. |
| 10,470,821 B2 | 11/2019 | Jaramaz et al. |
| 10,478,318 B2 | 11/2019 | Behzadi et al. |
| 10,499,996 B2 | 12/2019 | De Almeida |
| 10,537,388 B2 | 1/2020 | Jaramaz et al. |
| 10,603,115 B2 | 3/2020 | Van Der Walt et al. |
| 10,660,709 B2 | 5/2020 | Chaoui |
| 10,675,063 B2 | 6/2020 | Pavlovskaia et al. |
| 10,695,183 B2 | 6/2020 | Nelson |
| 10,716,580 B2 | 7/2020 | Berend et al. |
| 10,716,628 B2 | 7/2020 | McCabe et al. |
| 10,716,630 B2 * | 7/2020 | Krebs ................... A61B 5/055 |
| 10,729,558 B2 | 8/2020 | Macke et al. |
| 10,765,384 B2 | 9/2020 | Wollowick et al. |
| 10,772,685 B2 | 9/2020 | Erbe |
| 10,786,312 B2 | 9/2020 | Fanson et al. |
| 10,806,541 B2 | 10/2020 | Ross |
| 10,806,591 B2 | 10/2020 | Kovacs et al. |
| 10,863,995 B2 | 12/2020 | Nielsen et al. |
| 10,881,462 B2 | 1/2021 | Heavener et al. |
| 10,881,470 B2 | 1/2021 | Falardeau et al. |
| 10,932,866 B1 | 3/2021 | Bonny et al. |
| 10,945,801 B2 | 3/2021 | Borus et al. |
| 10,973,590 B2 | 4/2021 | Boddington et al. |
| 10,980,645 B2 | 4/2021 | Falardeau et al. |
| 10,991,070 B2 | 4/2021 | Saget et al. |
| 11,020,053 B2 | 6/2021 | Bailey et al. |
| 11,020,189 B2 | 6/2021 | Tao et al. |
| 11,026,811 B2 | 6/2021 | Sherman et al. |
| 11,071,596 B2 | 7/2021 | Ryan et al. |
| 11,160,609 B2 | 11/2021 | Otto et al. |
| 11,172,990 B2 | 11/2021 | Lang |
| 11,173,048 B2 | 11/2021 | Yadav et al. |
| 11,176,667 B2 | 11/2021 | Hladio et al. |
| 11,179,062 B2 | 11/2021 | Borja |
| 11,179,167 B2 | 11/2021 | Stone |
| 11,207,134 B2 | 12/2021 | Hafez et al. |

(56) References Cited

U.S. PATENT DOCUMENTS

| | | |
|---|---|---|
| 11,207,195 B2 | 12/2021 | Bushell et al. |
| 11,213,336 B2 | 1/2022 | Walter et al. |
| 11,229,519 B2 | 1/2022 | Radermacher et al. |
| 11,229,520 B2 | 1/2022 | Fanson et al. |
| 11,234,825 B2 | 2/2022 | Johannaber et al. |
| 11,241,285 B2 | 2/2022 | Viscardi et al. |
| 11,241,287 B2 | 2/2022 | Boettner |
| 11,259,816 B2 | 3/2022 | Otto et al. |
| 11,298,188 B2 | 4/2022 | Kehres et al. |
| 11,298,189 B2 | 4/2022 | Kelman et al. |
| 11,298,190 B2 | 4/2022 | Quaid, III |
| 11,311,339 B2 | 4/2022 | Jansen et al. |
| 11,351,007 B1 | 6/2022 | Meftah et al. |
| 11,369,437 B2 | 6/2022 | Walter et al. |
| 11,386,556 B2 | 7/2022 | Saget et al. |
| 11,413,095 B2 | 8/2022 | Hladio et al. |
| 11,432,945 B2 | 9/2022 | Viscardi et al. |
| 11,452,566 B2 | 9/2022 | Michael et al. |
| 11,464,574 B2 | 10/2022 | Haider et al. |
| 11,478,310 B2 | 10/2022 | Poltaretskyi et al. |
| 11,478,362 B2 | 10/2022 | Thompson et al. |
| 11,484,325 B2 | 11/2022 | Hafez et al. |
| 11,484,368 B2 | 11/2022 | Krebs et al. |
| 11,490,965 B2 | 11/2022 | Bischoff et al. |
| 11,534,185 B2 | 12/2022 | Dumpe et al. |
| 11,576,725 B2 | 2/2023 | Chav et al. |
| 11,602,395 B2 | 3/2023 | Lang |
| 11,602,443 B1 | 3/2023 | Cole et al. |
| 11,607,233 B2 | 3/2023 | Tikka |
| 11,612,503 B1 | 3/2023 | Cole et al. |
| 11,622,813 B2 | 4/2023 | Ferro et al. |
| 11,622,814 B2 | 4/2023 | Dees et al. |
| 11,622,862 B2 | 4/2023 | Van Der Wal et al. |
| 11,642,174 B2 | 5/2023 | Wollowick et al. |
| 11,666,447 B1 | 6/2023 | Trauner et al. |
| 11,678,992 B2 | 6/2023 | Servidio et al. |
| 11,690,682 B2 | 7/2023 | Wilkinson et al. |
| 11,701,182 B2 | 7/2023 | McCabe et al. |
| 11,707,333 B2 | 7/2023 | Merette et al. |
| 11,717,353 B2 | 8/2023 | Zuhars et al. |
| 11,730,601 B2 | 8/2023 | Beck et al. |
| 11,730,603 B2 | 8/2023 | Zappacosta et al. |
| 11,737,826 B2 | 8/2023 | De Souza et al. |
| 11,737,893 B2 | 8/2023 | Schipper et al. |
| 11,744,644 B2 | 9/2023 | Wilkinson et al. |
| 11,744,650 B2 | 9/2023 | Mahfouz |
| 11,771,504 B2 | 10/2023 | Kang et al. |
| 11,786,284 B2 | 10/2023 | Khosla et al. |
| 11,806,239 B2 | 11/2023 | Macke |
| 11,813,052 B2 | 11/2023 | Gupta et al. |
| 11,819,298 B2 | 11/2023 | Librot |
| 2002/0133162 A1 | 9/2002 | Axelson, Jr. et al. |
| 2004/0106916 A1* | 6/2004 | Quaid .................. A61B 34/71 606/1 |
| 2005/0148855 A1 | 7/2005 | Kienzle, III |
| 2005/0182320 A1 | 8/2005 | Stifter et al. |
| 2005/0187562 A1 | 8/2005 | Grimm et al. |
| 2008/0033571 A1 | 2/2008 | Tuke |
| 2008/0065085 A1 | 3/2008 | Couture et al. |
| 2010/0170362 A1 | 7/2010 | Bennett et al. |
| 2012/0071893 A1 | 3/2012 | Smith et al. |
| 2013/0060278 A1 | 3/2013 | Bozung et al. |
| 2013/0105577 A1 | 5/2013 | Hildreth et al. |
| 2013/0211792 A1 | 8/2013 | Kang et al. |
| 2014/0135773 A1 | 5/2014 | Stein et al. |
| 2014/0208578 A1 | 7/2014 | Linderman et al. |
| 2015/0119987 A1 | 4/2015 | Davignon et al. |
| 2015/0185846 A1 | 7/2015 | Otto et al. |
| 2016/0038161 A1 | 2/2016 | Gibson |
| 2016/0193051 A1 | 7/2016 | Budhabhatti et al. |
| 2016/0278868 A1 | 9/2016 | Berend et al. |
| 2016/0338776 A1 | 11/2016 | Jaramaz et al. |
| 2017/0065432 A1 | 3/2017 | Singh |
| 2017/0161434 A1 | 6/2017 | Naudi |
| 2017/0215967 A1 | 8/2017 | Spath |
| 2017/0348011 A1 | 12/2017 | Kourtis et al. |
| 2017/0360509 A1* | 12/2017 | Bonny ............... A61B 17/1703 |
| 2018/0344465 A1 | 12/2018 | McPherson et al. |
| 2019/0000561 A1 | 1/2019 | Decker et al. |
| 2019/0090952 A1 | 3/2019 | Bonny et al. |
| 2019/0175283 A1 | 6/2019 | Bonny et al. |
| 2019/0365481 A1 | 12/2019 | Otto et al. |
| 2020/0000527 A1 | 1/2020 | Cazal |
| 2020/0060766 A1 | 2/2020 | Hafez et al. |
| 2020/0074631 A1 | 3/2020 | Giancardo et al. |
| 2020/0077924 A1 | 3/2020 | Hladio et al. |
| 2020/0129311 A1 | 4/2020 | Singh et al. |
| 2020/0163721 A1 | 5/2020 | Aghazadeh |
| 2020/0222206 A1 | 7/2020 | Elliot |
| 2020/0281656 A1 | 9/2020 | Torabi et al. |
| 2020/0352654 A1 | 11/2020 | Van Der Walt et al. |
| 2020/0383796 A1 | 12/2020 | Johannaber et al. |
| 2021/0022808 A1 | 1/2021 | Lang |
| 2021/0038328 A1 | 2/2021 | Boisvert et al. |
| 2021/0052327 A1 | 2/2021 | Kuznik et al. |
| 2021/0059838 A1 | 3/2021 | Bodner |
| 2021/0093389 A1 | 4/2021 | Poltaretskyi et al. |
| 2021/0093390 A1 | 4/2021 | Poltaretskyi et al. |
| 2021/0128249 A1 | 5/2021 | Billard et al. |
| 2021/0145517 A1 | 5/2021 | Pierrepont et al. |
| 2021/0161681 A1 | 6/2021 | Nguyen et al. |
| 2021/0220054 A1 | 7/2021 | Parker et al. |
| 2021/0275227 A1 | 9/2021 | Park et al. |
| 2021/0327065 A1 | 10/2021 | Wright |
| 2022/0008131 A1 | 1/2022 | Sculco et al. |
| 2022/0031414 A1 | 2/2022 | Wright et al. |
| 2022/0039881 A1 | 2/2022 | Avisar et al. |
| 2022/0104881 A1 | 4/2022 | Otto et al. |
| 2022/0117755 A1 | 4/2022 | McGuan et al. |
| 2022/0125518 A1 | 4/2022 | Signoretti et al. |
| 2022/0160439 A1 | 5/2022 | Ryan et al. |
| 2022/0160440 A1 | 5/2022 | Jaramaz et al. |
| 2022/0175400 A1 | 6/2022 | Greber |
| 2022/0175453 A1 | 6/2022 | Xu et al. |
| 2022/0183757 A1 | 6/2022 | Caldera et al. |
| 2022/0192755 A1 | 6/2022 | Siccardi et al. |
| 2022/0202494 A1 | 6/2022 | Dressler et al. |
| 2022/0202503 A1 | 6/2022 | Dressler et al. |
| 2022/0218422 A1 | 7/2022 | Khurana et al. |
| 2022/0257145 A1 | 8/2022 | Hladio et al. |
| 2022/0296259 A1 | 9/2022 | Shah |
| 2022/0313443 A1 | 10/2022 | Keefer et al. |
| 2022/0323162 A1 | 10/2022 | Bonny et al. |
| 2022/0361955 A1 | 11/2022 | Signoretti et al. |
| 2022/0398817 A1 | 12/2022 | Chaoui et al. |
| 2023/0010852 A1 | 1/2023 | Cooper et al. |
| 2023/0013210 A1 | 1/2023 | Facchinello et al. |
| 2023/0056596 A1 | 2/2023 | Farley et al. |
| 2023/0068971 A1 | 3/2023 | Derouault et al. |
| 2023/0113848 A1 | 4/2023 | Chaoui et al. |
| 2023/0116074 A1 | 4/2023 | Grostefon et al. |
| 2023/0126955 A1 | 4/2023 | Jaramaz et al. |
| 2023/0131309 A1 | 4/2023 | Jaramaz et al. |
| 2023/0141368 A1 | 5/2023 | Donnelly et al. |
| 2023/0146371 A1 | 5/2023 | Gargac et al. |
| 2023/0157756 A1 | 5/2023 | Simoes et al. |
| 2023/0190139 A1 | 6/2023 | Godbey et al. |
| 2023/0190494 A1 | 6/2023 | Webb et al. |
| 2023/0200826 A1 | 6/2023 | McAuliffe |
| 2023/0240759 A1 | 8/2023 | Khare |
| 2023/0255691 A1 | 8/2023 | Blau et al. |
| 2023/0285080 A1 | 9/2023 | Hladio et al. |
| 2023/0285082 A1 | 9/2023 | Grammatopoulos et al. |
| 2023/0301719 A1 | 9/2023 | Murphy |

FOREIGN PATENT DOCUMENTS

| | | |
|---|---|---|
| EP | 2 556 802 A1 | 2/2013 |
| EP | 2 941 204 A1 | 11/2015 |
| JP | 2007-534351 A | 11/2007 |
| JP | 2011-217787 A | 11/2011 |
| JP | 2014-531920 A | 12/2014 |
| JP | 2016-505326 A | 2/2016 |
| KR | 20160010425 A | 1/2016 |

(56) References Cited

FOREIGN PATENT DOCUMENTS

| WO | WO-97/30652 A1 | 8/1997 |
|----|----------------|--------|
| WO | WO-2013/025814 A1 | 2/2013 |
| WO | WO-2014/145591 | 9/2014 |
| WO | WO-2016/089870 | 6/2016 |
| WO | WO-2017/204832 A1 | 11/2017 |
| WO | WO-2018/125834 A1 | 7/2018 |
| WO | WO-2018/169995 A1 | 9/2018 |
| WO | WO-2019/148154 A1 | 8/2019 |
| WO | WO-2019/202320 A1 | 10/2019 |
| WO | WO-2020/231656 A2 | 11/2020 |
| WO | WO-2022/126827 A1 | 6/2022 |
| WO | WO-2022/126828 A1 | 6/2022 |
| WO | WO-2022/173775 A1 | 8/2022 |
| WO | WO-2022/183719 A1 | 9/2022 |
| WO | WO-2023/059931 A1 | 4/2023 |
| WO | WO-2023/165568 A1 | 9/2023 |
| WO | WO-2023/197504 A1 | 10/2023 |
| WO | WO-2023/214036 A1 | 11/2023 |

OTHER PUBLICATIONS

International Search Report and Written Opinion for International Application No. PCT/US2017/041989, dated Oct. 17, 2017, 14 pages.

\* cited by examiner

SYSTEMS AND METHODS FOR GUIDING A REVISION PROCEDURE

CROSS-REFERENCE TO RELATED PATENT APPLICATIONS

This application is a continuation of U.S. application Ser. No. 17/134,774, filed Dec. 28, 2020, which is a continuation of U.S. application Ser. No. 16/923,192, filed Jul. 8, 2020, which is a continuation of U.S. application Ser. No. 15/649,416, filed Jul. 13, 2017, which claims priority to and the benefit of U.S. Provisional Application No. 62/363,037, filed Jul. 15, 2016, all of which are hereby incorporated by reference herein in their entireties.

BACKGROUND

The present disclosure is related to robotic assisted orthopedic surgeries, and in particular, to robotic assisted revision surgeries.

Currently, surgeons perform revision surgeries, such as revision knee and hip procedures manually. This manual surgery is not always accurate, is difficult to perform, and could result in greater bone loss than desired, which lessens the strength and integrity of the bone. The limited access and occurrence of inaccurate cutting, removing of the implant, and cementation of the implant can cause significant bone loss. During the procedure, surgeons may use a chisel and micro saw to manually dissect the implant. The surgeon has to perform this approach very slowly in order to preserve the bone. The timing of the surgery, however, may be critical for the patient due to duration of the anesthesia. In addition, performing such a procedure requires significant training.

SUMMARY OF THE INVENTION

According to one exemplary embodiment, there is a method for performing a revision surgery using a robotic-assisted surgery system. The method includes determining, by a processing circuit associated with a computer, information related to an interface area between an implant component and a bone on which the implant component is implanted. The method further includes generating, by the processing circuit, a planned virtual boundary in a representation of the implant component and the bone, the planned virtual boundary associated with a portion of the interface area to be removed, and based at least in part on the information related to the interface area. The method further includes tracking, by a navigation system associated with the computer, movement in the physical space of a cutting tool such that movement of the cutting tool is correlated with movement of a virtual tool, and providing a constraint on the cutting tool while the cutting tool removes the portion of the interface area, the constraint based on a relationship between the virtual tool and the planned virtual boundary. The portion of the interface area is removed to remove the implant component from the bone.

In some embodiments, determining information related to an interface area comprises receiving images of the bone and the implant component implanted thereon. In some embodiments, the images were obtained in relation to a primary procedure during which the implant component was implanted on the bone. In some embodiments, the images are received by at least one imaging modality from a group consisting of: CT, x-ray, fluoroscope, MRI, ultrasound, video camera, and tracked markers. In some embodiments, determining information related to an interface area comprises digitizing the interface area with a tracked probe.

In some embodiments, the method further includes receiving an input for adjusting the virtual boundary relative to the representation of the implant and the bone. In some embodiments, the virtual boundary is a haptic boundary and wherein providing the constraint comprises providing haptic feedback to the cutting tool. In some embodiments, the virtual boundary is an autonomous control boundary and wherein providing the constraint comprises autonomously controlling the surgical tool to remain within the control boundary. In some embodiments, the cutting tool is one or more tools from the group consisting of but not limited to: a planar saw, a curved saw, a laser, waterjet, ultrasound vibrations, and a burr.

In some embodiments, the method further includes determining, by the processing circuit, information related to at least one of a size, a quantity, and a location of bone defects near the interface which require an augment. In some embodiments, the information is determined pre-operatively. In some embodiments, the information is determined by digitizing the bone defects with a tracked probe.

In some embodiments, the method further includes using a video camera to obtain an image of the bone after the implant component has been removed; and generating a bone model of the bone based on the image for planning replacement of the implant component.

In some embodiments, the method further includes determining a desired pose of a replacement implant component to be implanted on the bone. In some embodiments, the method further includes determining, by the processing circuit, a second planned virtual boundary in a representation of the bone representing one or more cuts in the bone to prepare the bone to receive the replacement implant. In some embodiments, the method further includes providing a constraint on the cutting tool while the cutting tool performs the one or more cuts to prepare the bone, the constraint based on a relationship between the virtual tool and the second planned virtual boundary.

In another exemplary embodiment there is a system for performing revision surgery. The system includes a robotic system comprising an articulated arm and a surgical tool coupled to the articulated arm, a navigation system configured to characterize movement of at least one of the articulated arm, the surgical tool, and a portion of the patient's anatomy for revision, and a processor operatively coupled to the robotic system and the navigation system. The processor is configured to determine information related to an interface area between an implant component and a bone on which the implant component is implanted generate a planned virtual boundary based upon a representation of the implant component and the bone, the planned virtual boundary associated with a portion of the interface area to be removed, and based at least in part on the information related to the interface area; track, using the navigation system, movement in the physical space of the cutting tool such that movement of the cutting tool is correlated with movement of a virtual tool; and provide a constraint on the cutting tool while the cutting tool removes the portion of the interface area, the constraint based on a relationship between the virtual tool and the planned virtual boundary.

In some embodiments, the system further includes an imaging system operatively coupled to the processor for determining the information related to the interface area, wherein the imaging system comprises at least one of the imaging modalities from the group consisting of: CT, x-ray, fluoroscope, MM, ultrasound, video camera, and tracked markers. In some embodiments, the system further includes a tracked probe for digitizing the interface area.

In some embodiments, the surgical tool coupled to the articulated arm comprises an end effector. The end effector includes at least one flexible bending element capable of movement in two degrees of freedom, the bending element comprising a distal end, a proximal end and an internal channel; a shaft coupled to the proximal end of the flexible bending element and configured to secure the end effector to a surgical system; and a motor housed in the shaft and coupled to the cutting tool to provide power to the cutting tool. A cutting element is coupled to the distal end of the flexible bending element.

In an embodiment, a robotic system is used to assist in a knee or hip revision procedure. The robotic system may include a navigation system to register real bone to pre-scan CT images and precisely guide a robot arm to navigate through the patient anatomical space. The robotic system may have haptic capability, wherein the user can shape the haptic volume based on patient anatomy to protect the important bone structure and soft tissues (such as ligaments, nerves, and veins). The system may further include a flexible end effector, having multiple degrees of freedom and can be bent 90 degrees in any direction to allow the cutting tool, attached to the flexible arm, to access small area to dissect the bone implant. The system may have a large database which saves patient bone models and implant models and planning history during their primary knee or hip procedure, with the information being available for use in revision cases.

In another embodiment, the robotic system, using patient's previous/primary knee and hip information, can assist in revision cases by using a patient's previous/primary knee and hip implant model to create a revision haptic boundary to haptically guide the revision procedure; using a patient's previous/primary knee and hip bone model to register the bone to robot coordinate, wherein the patient does not need to take an extra CT image for the revision case; and using patient's previous/primary knee and hip planning information to identify the relative position between bone and implant in the revision case, wherein there is no relative motion between bone and implant, the implant surface is used to register the bone to robot coordinate.

In some embodiments, the robotic system creates a customized revision haptic boundary to protect overcutting of the bone and minimizing the bone lost during the revision procedure.

In some embodiments, the robotic system, based on the primary knee and hip implant model, precisely creates the revision haptic boundary around the primary implant to constraint the cutting tool and minimize overcutting the bone. In some embodiments, one of the following methods is used to register the implant and bone to primary knee and hip CT image during the revision: a trackable probe to digitize the implant surface and then register the bone to primary CT image; taking a few fluoroscopic images; and/or attaching a camera or optical sensor to the robot to scan the implant surface and then register it to the primary CT bone model. In some embodiments, the robotic system includes a dexterous flexible end effector system, the flexible end effector having multiple degrees of freedom and bendable in omni-direction to allow robot cut bone with constraint access space, and the flexible end effector carrying a high-speed rotating burr for cutting bone. In some embodiments, a video camera or ultrasound device is used to create an initial bone or implant model and/or to register the bone with the bone model.

BRIEF DESCRIPTION OF THE DRAWINGS

The accompanying drawings, which are incorporated and constitute a part of this specification, illustrate several embodiments that, together with the description, serve to explain the principles and features of the present disclosure.

DETAILED DESCRIPTION

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

The present disclosure introduces a robotic assisted approach to support a revision procedure of a joint, such as the knee joint or the hip joint, by allowing precise removal of a primary implant with minimal bone loss and while reducing the time needed to remove the primary implant. When bone loss is minimized, the number of revision procedures that may be performed on an individual patient during their lifetime increases.

Though the present disclosure makes reference to the knee and the hip joint, and revisions for the knee and the hip, the systems and methods disclosed herein are equally applicable to other orthopedic revision surgeries for other bones or joints, including, but not limited to, the shoulder, the wrist, the ankle, the spine, etc.

The robotic-assisted surgery system of the present disclosure is designed to assist revision procedures to minimize the amount of bone removed and/or the damage on the bone. The robotic assisted surgery system is also designed to shorten the lengthy learning curve for the surgeon for performing a revision procedure. The robotic assisted surgery system may help in reducing the time to perform a revision, and allow a better recovery of the bone because the bone may be less "damaged" as a result of the use of the robotic system. In addition, the disclosure addresses one major issue of the previously used systems which is visibility of the progress of the breakdown of the interface. In certain embodiments, the robotic system can provide the user with a plan to remove the interface entirely, and then help the user execute the plan while providing feedback during the removal process.

Exemplary Robotic System

Figure 1:
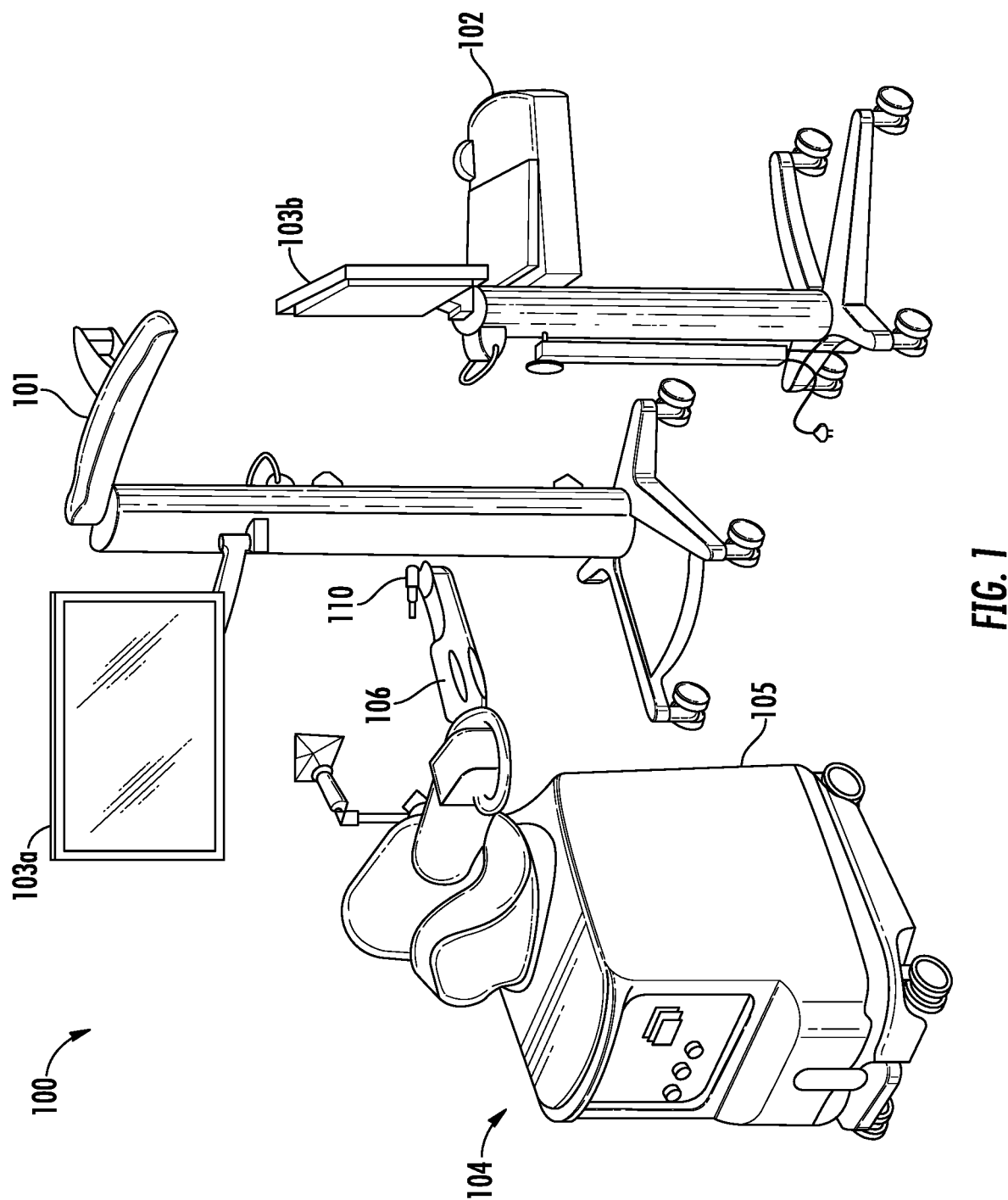
FIG. 1 illustrates a perspective view of an embodiment of a surgical system, according to an exemplary embodiment.

Various features of a robotic assisted surgery system and methods according to the present disclosure will now be described in greater detail. FIG. 1 provides a schematic diagram of an exemplary computer-assisted surgery (CAS) system 100, in which processes and features associated with certain disclosed embodiments may be implemented. Surgical system 100 may be configured to perform a wide variety of orthopedic surgical procedures such as, for example, knee revision procedures. Surgical system 100 includes a tracking system 101, computing system 102, one or more display devices 103a, 103b, and a robotic system 104. It should be appreciated that system 100, as well as the methods and processes described herein, may be applicable to many different types of joint revision procedures. Although certain disclosed embodiments may be described with respect to knee revision procedures, the concepts and methods described herein may be applicable to other types of orthopedic surgeries, such as hip revisions, shoulder revision procedures, and other types of orthopedic procedures. Further, surgical system 100 may include additional elements or fewer elements than those described, to aid in surgery (e.g., surgical bed, etc.).

Robotic system 104 can be used in an interactive manner by a surgeon to perform a surgical procedure, such as a revision procedure, on a patient. As shown in FIG. 1, robotic system 104 includes a base 105, an articulated arm 106, a force system (not shown), and a controller (not shown). A surgical tool 110 (e.g., an end effector having an operating member, such as a saw, reamer, or burr) may be coupled to the articulated arm 106. The surgeon can manipulate the surgical tool 110 by grasping and manually moving the articulated arm 106 and/or the surgical tool 110.

The force system and controller are configured to provide a cutting restraint guide via control or guidance to the surgeon during manipulation of the surgical tool. The force system is configured to provide at least some force to the surgical tool via the articulated arm 106, and the controller is programmed to generate control signals for controlling the force system. In one embodiment, the force system includes actuators and a back-driveable transmission that provide haptic (or force) feedback to constrain or inhibit the surgeon from manually moving the surgical tool beyond predefined haptic boundaries defined by haptic objects as described, for example, in U.S. Pat. No. 8,010,180 and/or U.S. patent application Ser. No. 12/654,519 (U.S. Patent Application Pub. No. 2010/0170362), filed Dec. 22, 2009, each of which is hereby incorporated by reference herein in its entirety. The force system and controller may be housed within the robotic system 104. In some embodiments, cutting restraint or guidance is provided though a handheld manipulator or handheld robotic device, such as described in U.S. Pat. No. 9,399,298 entitled "Apparatus and Method for Providing an Adjustable Positive Stop in Space," U.S. Pat. No. 9,060,794 entitled "System and Method for Robotic Surgery," and U.S. Patent Publication No. 2013/0060278 entitled "Surgical instrument including housing, a cutting accessory that extends from the housing and actuators that establish the position of the cutting accessory relative to the housing," each of which is incorporated herein by reference in its entirety.

Tracking system 101 is configured to determine a pose (i.e., position and orientation) of one or more objects during a surgical procedure to detect movement of the object(s). For example, the tracking system 101 may include a detection device that obtains a pose of an object with respect to a coordinate frame of reference of the detection device. As the object moves in the coordinate frame of reference, the detection device tracks the pose of the object to detect (or enables the surgical system 100 to determine) movement of the object. As a result, the computing system 102 can capture data in response to movement of the tracked object or objects. Tracked objects may include, for example, tools/instruments, patient anatomy, implants/prosthetic devices, and components of the surgical system 100. Using pose data from the tracking system 101, the surgical system 100 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on a surgical controller and/or the computer device of the robotic system 104. For example, utilizing pose data from the tracking system 101, the surgical system 100 is able to associate the physical anatomy, such as the patient's tibia, with a representation of the anatomy (such as an image displayed on the display device 103). Based on tracked object and registration data, the surgical system 100 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MM and CT, are registered), image-to-physical space registration (e.g., image-to-patient registration where a digital data set of a patient's anatomy obtained by conventional imaging techniques is registered with the patient's actual anatomy), combined image-to-image and image-to-physical-space registration (e.g., registration of preoperative CT and MM images to an intraoperative scene), and/or registration using a video camera or ultrasound. The computing system 102 may also include a coordinate transform process for mapping (or transforming) coordinates in one space to those in another to achieve spatial alignment or correspondence. For example, the surgical system 100 may use the coordinate transform process to map positions of tracked objects (e.g., patient anatomy, etc.) into a coordinate system used by a process running on the computer of the haptic device and/or a surgical controller. As is well known, the coordinate transform process may include any suitable transformation technique, such as, for example, rigid-body transformation, non-rigid transformation, affine transformation, and the like. In some embodiments, the video camera includes a tracker and a scan of the bone to obtain a model and register the model. For example, an initial 3D model can be created and automatically registered. In some embodiments, the video camera can be used to register a 3D model corresponding to a CT scan. According to some embodiments, a video camera or ultrasound can be used for both initial model creation and registration.

The tracking system 101 may be any tracking system that enables the surgical system 100 to continually determine (or track) a pose of the relevant anatomy of the patient. For example, the tracking system 101 may include a non-mechanical tracking system, a mechanical tracking system, or any combination of non-mechanical and mechanical tracking systems suitable for use in a surgical environment.

The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

Computing system 102 may be communicatively coupled to tracking system 101 and may be configured to receive tracking data from tracking system 101. Based on the received tracking data, computing system 102 may determine the position and orientation associated with one or more registered features of the surgical environment, such as surgical tool 110 or portions of the patient's anatomy. Computing system 102 may also include surgical planning and surgical assistance software that may be used by a surgeon or surgical support staff during the surgical procedure. For example, during a joint replacement procedure, computing system 102 may display images related to the surgical procedure on one or both of the display devices 103a, 103b.

Computing system 102 (and/or one or more constituent components of surgical system 100) may include hardware and software for operation and control of the surgical system 100. Such hardware and/or software is configured to enable the system 100 to perform the techniques described herein.

Figure 2:
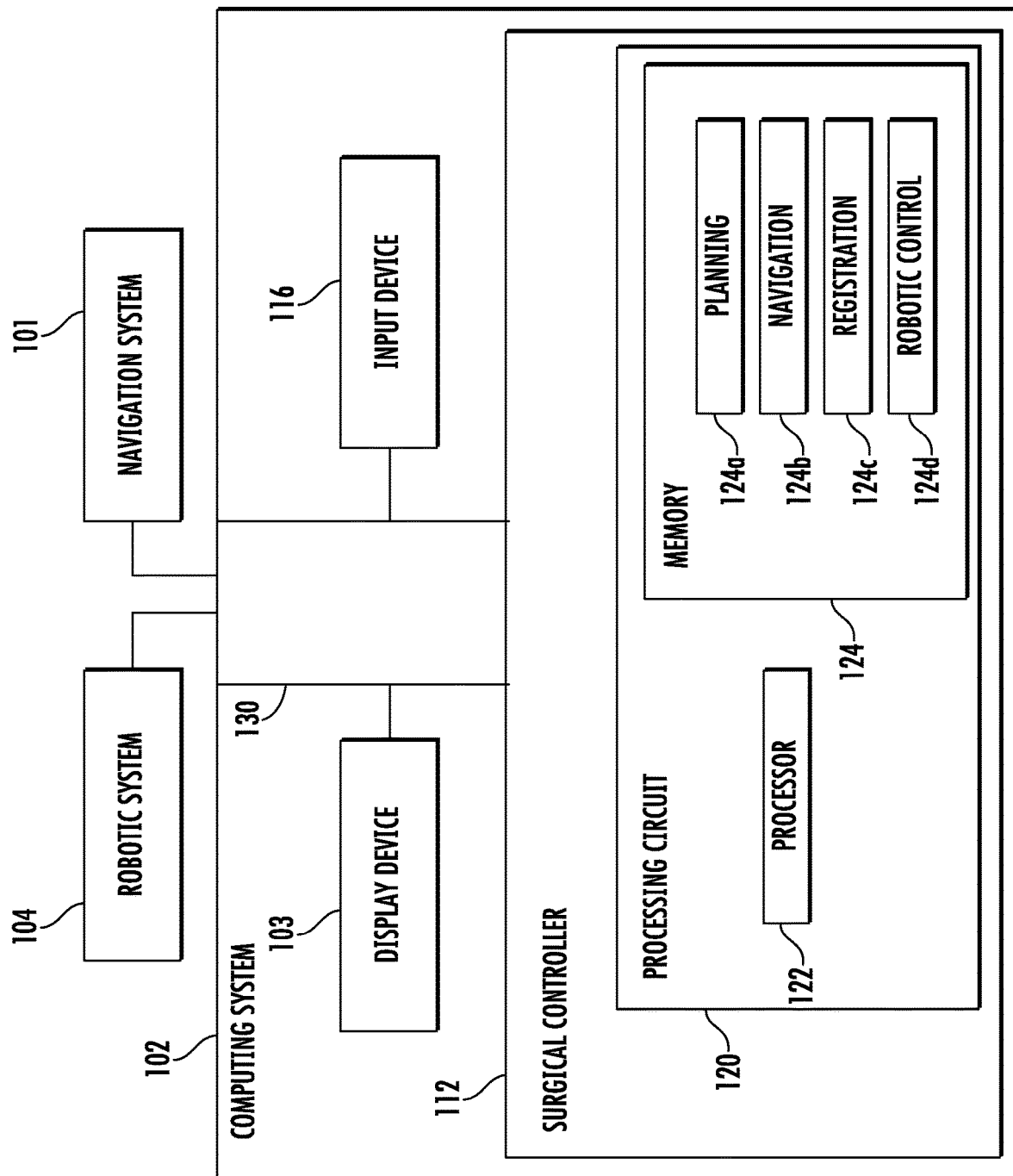
FIG. 2 illustrates a block diagram of a computing system according to an exemplary embodiment.

FIG. 2 illustrates a block diagram of the computing system 102 according to an exemplary embodiment. The computing system 102 includes a surgical controller 112, a display device 103 (e.g., display devices 103a and 103b), and an input device 116.

The surgical controller 112 may be any known computing system but is preferably a programmable, processor-based system. For example, the surgical controller 112 may include a microprocessor, a hard drive, random access memory (RAM), read only memory (ROM), input/output (I/O) circuitry, and any other known computer component. The surgical controller 112 is preferably adapted for use with various types of storage devices (persistent and removable), such as, for example, a portable drive, magnetic storage, solid state storage (e.g., a flash memory card), optical storage, and/or network/Internet storage. The surgical controller 112 may comprise one or more computers, including, for example, a personal computer or a workstation operating under a suitable operating system and may include a graphical user interface (GUI).

Still referring to FIG. 2, in an exemplary embodiment, the surgical controller 112 includes a processing circuit 120 having a processor 122 and memory 124. Processor 122 can be implemented as a general purpose processor executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit), a group of processing components, or other suitable electronic processing components. Generally, a processor will receive instructions and data from a read only memory or a random access memory or both. Memory 124 (e.g., memory, memory unit, storage device, etc.) comprises one or more devices (e.g., RAM, ROM, Flash-memory, hard disk storage, etc.) for storing data and/or computer code for completing or facilitating the various processes described in the present application. Memory 124 may be or include volatile memory or non-volatile memory. Memory 124 may include database components, object code components, script components, or any other type of information structure for supporting the various activities described in the present application. According to an exemplary embodiment, memory 124 is communicably connected to processor 122 and includes computer code for executing one or more processes described herein. The memory 124 may contain a variety of modules, each capable of storing data and/or computer code related to specific types of functions. In one embodiment, memory 124 contains several modules related to surgical procedures, such as a planning module 124a, a navigation module 124b, a registration module 124c, and a robotic control module 124d.

Alternatively, or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). Accordingly, the computer storage medium may be tangible and non-transitory.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a tablet, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an embodiment of the subject matter described in this specification, or any combination of one or more such back end, middleware, or front end components. The components of the system can be interconnected by any form or medium of digital data communication, e.g., a communication network.

Referring to the embodiment of surgical system 100 depicted in FIG. 2, the surgical controller 112 further includes a communication interface 130. The communication interface 130 of the computing system 102 is coupled to a computing device (not shown) of the robotic system 104 via an interface and to the tracking system 101 via an interface. The interfaces can include a physical interface and a software interface. The physical interface of the communication interface 130 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). The software interface may be resident on the surgical controller 112, the computing device (not shown) of the robotic system 104, and/or the tracking system 101. In some embodiments, the surgical controller 112 and the computing device (not shown) are the same computing device. The software may also operate on a remote server, housed in the same building as the surgical system 100, or at an external server site.

Computing system 102 also includes display device 103. The display device 103 is a visual interface between the computing system 102 and the user. The display device 103 is connected to the surgical controller 112 and may be any device suitable for displaying text, images, graphics, and/or other visual output. For example, the display device 103 may include a standard display screen, a touch screen, a wearable display (e.g., eyewear such as glasses or goggles), a projection display, a head-mounted display, a holographic display, and/or any other visual output device. The display device 103 may be disposed on or near the surgical controller 112 (e.g., on the cart as shown in FIG. 1) or may be remote from the surgical controller 112 (e.g., mounted on a stand with the tracking system 101). The display device 103 is preferably adjustable so that the user can position/reposition the display device 103 as needed during a surgical procedure. For example, the display device 103 may be disposed on an adjustable arm (not shown) or to any other location well-suited for ease of viewing by the user. As shown in FIG. 1 there may be more than one display device 103 in the surgical system 100.

The display device 103 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like.

In addition to the display device 103, the computing system 102 may include an acoustic device (not shown) for providing audible feedback to the user. The acoustic device is connected to the surgical controller 112 and may be any known device for producing sound. For example, the acoustic device may comprise speakers and a sound card, a motherboard with integrated audio support, and/or an external sound controller. In operation, the acoustic device may be adapted to convey information to the user. For example, the surgical controller 112 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a tone to indicate that a surgical cutting tool is nearing a critical portion of soft tissue or is approaching a virtual control boundary.

To provide for other interaction with a user, embodiments of the subject matter described in this specification can be implemented on a computer having input device 116 that enables the user to communicate with the surgical system 100. The input device 116 is connected to the surgical controller 112 and may include any device enabling a user to provide input to a computer. For example, the input device 116 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, input device 116 can allow the user manipulate a virtual control boundary. Other kinds of devices can be used to provide for interaction with a user as well, for example, feedback provided to the user can be any form of sensory feedback, e.g., visual feedback, auditory feedback, or tactile feedback, and input from the user can be received in any form, including acoustic, speech, or tactile input. In addition, a computer can interact with a user by sending documents to and receiving documents from a device that is used by the user, for example, by sending web pages to a web browser on a user's client device in response to requests received from the web browser.

General surgical planning and navigation to carry out the exemplary methods described above, and including haptic control and feedback as described in connection with surgical system 100, may be performed by a computerized surgical system such as that described in U.S. Pat. No. 8,010,180 "Haptic Guidance System and Method" to Quaid et al., which is incorporated herein by reference in its entirety.

Virtual Objects for Robotic Assisted Surgery

Figure 3A:
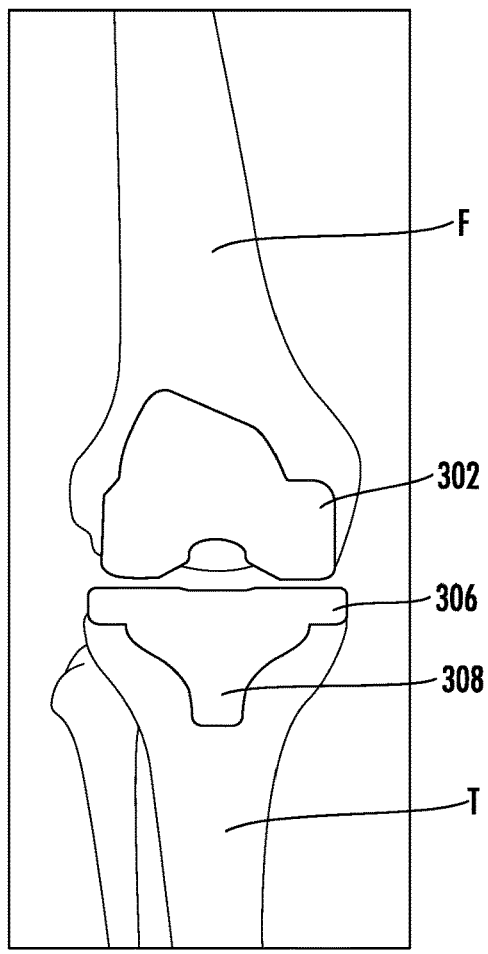
FIGS. 3A-3B illustrate an X-ray showing a femur, a tibia, a femoral implant and a tibia implant, according to an exemplary embodiment.
Figure 3B:
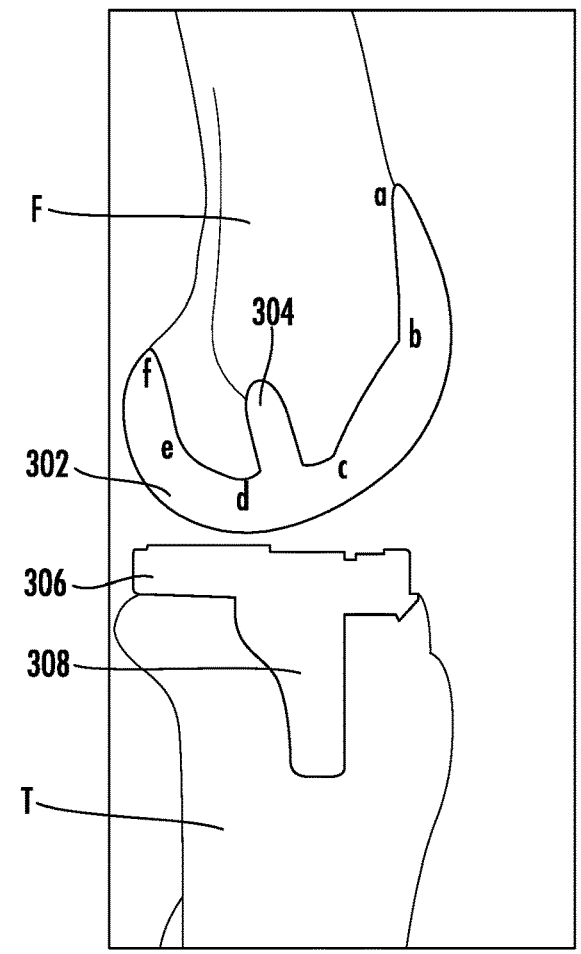

FIGS. 3A-3B illustrate an example x-ray showing a femur (F), a tibia (T), a femoral implant 302 and a tibial implant 306, according to an exemplary embodiment. While an x-ray image is shown in FIGS. 3A and 3B, other images can be acquired and used to generate bone models using any of a variety of imaging techniques (e.g., CT, MM, ultrasound, video camera, etc.) As shown, the femoral implant 302 includes projections, such as a peg 304 extending into the femur F, and the tibial implant 306 includes, for example, a keel 308. During implantation, cement is provided under flat portions of a baseplate of the tibial implant 306 and along flat surfaces of the femoral implant 302. In some embodiments, the femoral implant 302 includes 5 flat portions, portion ab, portion bc, portion cd, portion de, and portion ef. In some embodiments, cement is located on some or all of the flat portions of the femoral implant 302. During a revision surgery, the implants 302 and 306 must be cut around for removal, including the peg 304 and the keel 308. However, over time, the keel 308 may have ingrowth with the tibia T that may cause bone pieces to break off during removal. To reduce the bone loss during removal, an image of the implant (e.g., obtained by CT, Mill, video, ultrasound, etc.), can be used to create a model of the bones and the implants for generation of surgical plans for removal. In some embodiments, a tracking probe can be used to probe, for example, areas near points a, b, c, d, e and f or along the edges of portions ab, bc, cd, de and ef to generate a model of the interface between the femoral implant 302 and the bone.

Figure 4:
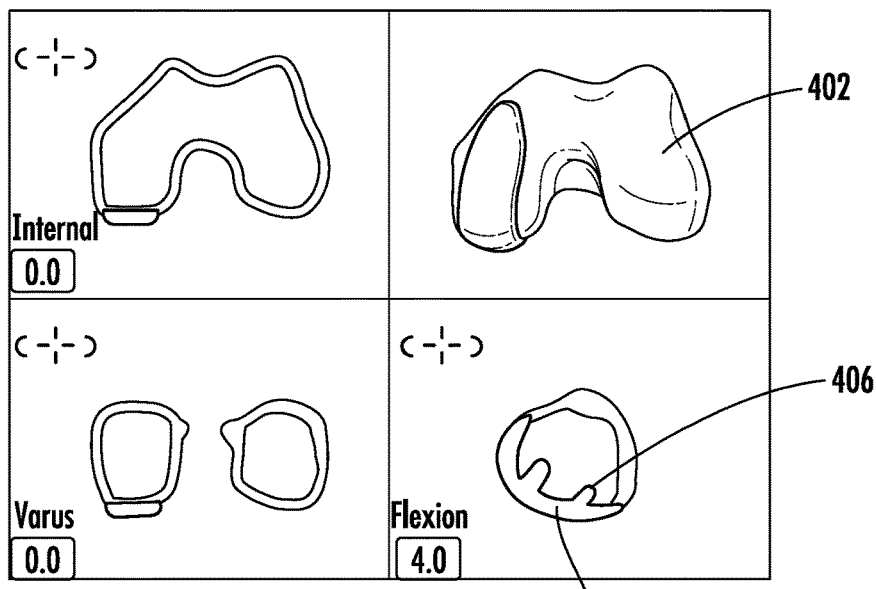
FIG. 4 illustrates a bone model and implant model as shown on a user interface during a primary partial knee procedure.

FIG. 4 illustrates a graphical user interface showing a model of a bone 402 and a model of an implant 404 during a primary partial knee procedure, according to an exemplary embodiment. Specifically, FIG. 4 depicts a distal end of a femur 402 that received the femoral implant 404. As shown, the femoral implant 404 includes elongated projections 406 (e.g., pegs, screws, keels, etc.) that were received by apertures in the femur. The elongated projections 406 further secure the femoral implant 404 to the bone 402 and help resist movement between the implant 404 and the bone 402. The bone may have been prepared with keels (not shown), which interface with keels on the femoral implant 404 to improve security between the bone 402 and the implant 404. The model may allow a user to modify the view of the implant model through rotation of the model or selection of different viewing modes. In some embodiments, the model may allow a user to view different cross sectional views of the implant, bone, or a combination thereof. In some embodiments, the model may also provide information to aid in planning a revision surgery (e.g., size, location, material, etc.).

The surgical system 100 of FIG. 1 may be configured to establish a virtual control object associated with the current prosthetic implant component and associated with or relative to one or more features of a patient's anatomy. The surgical system 100 may be configured to create a virtual representation of a surgical site that includes, for example, virtual representations of a patient's anatomy, a surgical instrument to be used during a surgical procedure, a probe tool for registering other objects within the surgical site, and any other object associated with a surgical site.

In addition to physical objects, the surgical system 100 may be configured to generate virtual objects that exist in software and may be useful during the performance of a surgical procedure. For example, surgical system 100 may be configured to generate virtual boundaries or virtual control boundaries, that correspond to a surgeon's plan for preparing a bone, such as boundaries defining areas of the bone that the surgeon plans to cut, remove, or otherwise alter. In the case of a revision surgery, the virtual boundaries may correspond to a surgeon's plan for removing the cement and the necessary bone making up the interface between an implanted prosthetic component and the bone on which it is implanted. Alternatively, or additionally, surgical system 100 may define virtual objects that correspond to a desired path or course over which a portion of surgical tool 110 (e.g., end effector 200) should navigate to perform a particular task.

The surgical system 100 may also be configured to generate virtual objects or boundaries as part of a specific surgical plan. In some embodiments, the surgical plan is generated based on a database of implants where the surgical plans correspond to registered models of implants or bones. If an implant is known in the database, a surgical plan can be proposed to the user. The surgical plan may include which tools should be used, what access is needed to get around parts of the implant, virtual boundaries, etc. The proposed surgical plan may include virtual objects around keels and pegs, and may propose tool changes for cutting around these implant features. In some embodiments, the surgical plans are modifiable by the user including, but not limited to, the tools to be used, the access needed, the shape of the implant and the virtual boundaries. In some embodiments, a generic surgical plan can be automatically modified based on a model capture of the patient's anatomy or implant, or on the specific implant.

Virtual boundaries and other virtual objects may define a point, line, or surface within a virtual coordinate space (typically defined relative to an anatomy of a patient) that serves as a boundary at which a constraint is provided to a surgical instrument when the tracked position of the surgical instrument interacts with the virtual boundary or object. In some embodiments, the constraint is provided through haptic or force feedback. For example, as the surgeon performs a bone cutting operation, a tracking system of the surgical system 100 tracks the location of the cutting tool and, in most cases, allows the surgeon to freely move the tool in the workspace. However, when the tool is in proximity to a virtual boundary (that has been registered to the anatomy of the patient), surgical system 100 controls the force feedback system to provide guidance that tends to constrain the surgeon from penetrating the virtual boundary with the cutting tool. For example, a virtual boundary may be associated with the geometry of a virtual model of a prosthetic implant, and the haptic guidance may comprise a force and/or torque that is mapped to the virtual boundary and experienced by the surgeon as resistance to constrain tool movement from penetrating the virtual boundary. Thus, the surgeon may feel as if the cutting tool has encountered a physical object, such as a wall. Accordingly, the force feedback system of the surgical system 100 communicates this information to the surgeon regarding the location of the tool relative to the virtual boundary, and provides physical force feedback to guide the cutting tool during the actual cutting process. In this manner, the virtual boundary functions as a virtual cutting guide. The force feedback system of the surgical system 100 may also be configured to limit the user's ability to manipulate the surgical tool. The robotic system or manual tools could be attached to the implant to measure an applied force for removal. Monitoring the position of the implant with respect to the bone and the force applied could give the surgeon an indication of the ease of removal. This may indicate additional cutting is required to minimize unintentional bone loss. In some embodiments, the virtual boundaries define autonomous cutting controls allowing a surgical robot to perform all or some of the steps of the surgical plan autonomously. In some embodiments, the virtual boundaries define a combination of autonomous and manual cutting boundaries. In some embodiments, when using autonomous cutting controls, feedback can be used to indicate contact is made with the implant (e.g., contact made with a peg when the tool is cutting along a flat interface surface) and the surgical plan or boundaries could be adjusted to avoid the portion of the implant based on the feedback. For example, this may be particularly useful where a shape of a keel is not known or identifiable prior to beginning cutting, so the original boundaries do not take the keel into account. A surgical plan or virtual boundaries could be modified based on detected differences in the surgical plan and/or virtual boundary and the keel. In some embodiments, the virtual boundaries correspond to haptic boundaries defining a haptic object. In some embodiments, the haptic boundary is configured to provide haptic feedback when the haptic boundary is encountered. The haptic boundary can result in haptic feedback that is tactile, audible, visual, olfactory (i.e., smell), or other mean of providing feedback.

In some embodiments, the rendering application also creates a virtual object (not shown) that represents a pathway from a first position to a second position. For example, the virtual object may include a virtual guide wire (e.g., a line) defining a pathway from a first position (e.g., a position of a tool in physical space used with the surgical system 100) to a second position that includes a target (e.g., a target object such as the virtual object). The virtual object may be activated so that movement of the tool is constrained along the pathway defined by the virtual object. The surgical system 100 may deactivate the object when the tool reaches the second position and activates the target object (e.g., the virtual object). The tool may be automatically placed in a control, such as haptic control, (or burring) mode when the object is activated. In a preferred embodiment, the object may be deactivated to enable the tool to deviate from the pathway. Thus, the user can override the guidance associated with the object to deviate from the guide wire path and maneuver the tool around untracked objects (e.g., screws, retractors, lamps, etc.) that may not be accounted for when the virtual guide wire is generated.

In the control mode, the robotic system 104 is configured to provide guidance to the user during a surgical activity such as bone preparation. In one embodiment, the rendering application may include the virtual object defining a cutting volume on the tibia T. The virtual object may have a shape that substantially corresponds to a shape of a surface of a tibial component such as when preparing for implantation. In revision surgery, the virtual object may have a shape that substantially corresponds to a shape of the interface between, for example, the tibial component and the tibia on which it is implanted or the path for bone removal to be followed. The robotic system 104 may enter the control mode automatically, for example, when the tip of the tool approaches a predefined point related to a feature of interest. In some embodiments, the tool can be disabled whenever the tool is outside the virtual object. In another embodiment, the tool can be disabled unless the robotic system 104 is generating control feedback forces.

In operation, the surgical system 100 may be used for surgical planning and navigation. In addition to preparing a revision surgery, the surgical system 100 may be used, for example, to perform a knee replacement procedure or other joint replacement procedure involving installation of an implant. The implant may include any implant or prosthetic device, such as, for example, a total knee implant; a unicondylar knee implant; a modular knee implant; implants for other joints including hip, shoulder, elbow, wrist, ankle, and spine; and/or any other orthopedic and/or musculoskeletal implant, including implants of conventional materials and more exotic implants, such as orthobiologics, drug delivery implants, and cell delivery implants.

Robotic Revision Surgery

Revision surgery, such as knee revision, is a complex procedure and requires a very high level of expertise. There are several reasons that make the procedure more complex. The surgeon has to remove the original implant, which may be cemented or uncemented. The implant could have bone grown into it, and while removing the original implant, the surgeon has to try and conserve as much bone as possible. Furthermore, the implant(s) may include surfaces, keels, pegs, screws, or other components that need to be cut around, or through. In some embodiments, the implant may be multiple implants that individually need to be cut around and removed. Surgeons have to ensure that most of the bonds between the cement and the bone and/or between the implant and the bone are broken, resulting in a time consuming and complex process. Pre-existing solutions requires surgeons to chip away at the interface of bone-implant or bone-cement with manual or powered instruments. These include osteotomes, gigli saws and punches. Powered instrumentation is also available, for example power saws and burrs or ultrasonic devices. Despite attempts to preserve bone, there is always some amount of bone loss, and the surgeon must accurately fill in all the bone defects due to bone loss during removal of the implant. There may also be pre-existing bone defects that require attention after removal of the implant. The robotic system and specialized instrumentation of the present disclosure can help to resolve some of the issues faced during explantation.

The need for a revision can include, for example, infections, misalignment, and wear. In knee revision due to infection, the surgery may be a two stage surgery. In the first stage, the infected implant is removed, and the wound is cleaned. A spacer block is added to the joint and the wound is closed. The second stage removes the spacer and adds the new revision implant.

Figure 5A:
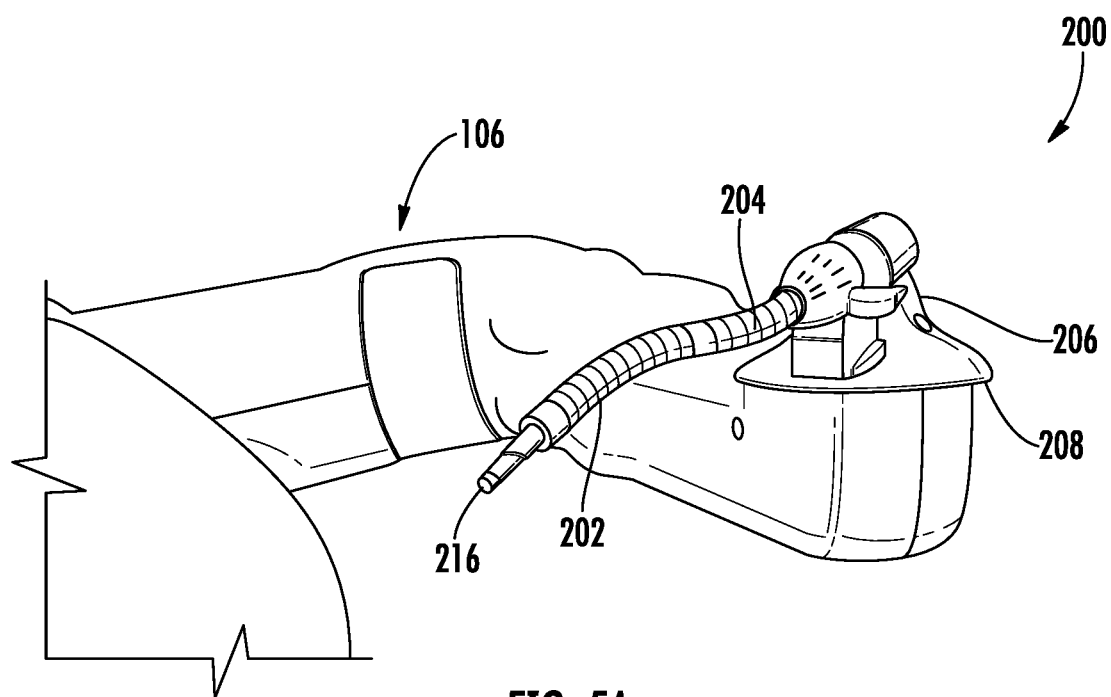
FIG. 5A illustrates a flexible end effector used with the surgical system of FIG. 1, according to an exemplary embodiment.
Figure 5B:
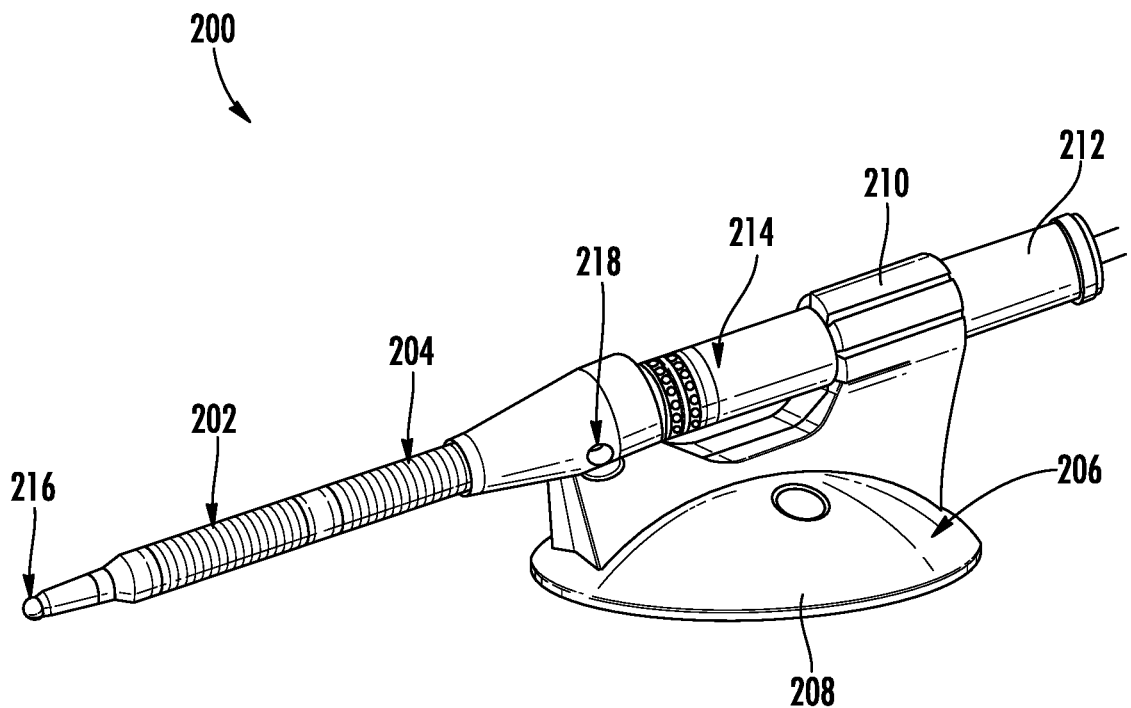
FIG. 5B illustrates the flexible end effector of FIG. 5A, according to an exemplary embodiment.
Figure 5C:
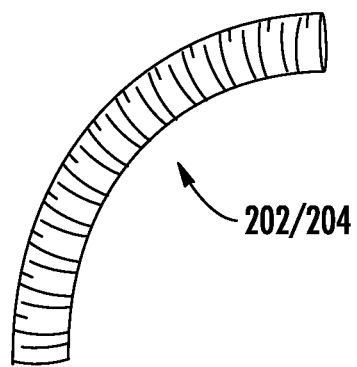
FIG. 5C illustrates a close up view of a flexible portion of the flexible end effector of FIG. 5A, according to an exemplary embodiment.

The present disclosure addresses the previously-faced issues of knee and/or hip revision by using a robotic-assisted approach. The present disclosure also describes a flexible end effector carrying a high-speed cutting burr. The flexible end effector is very dexterous to allow access to small areas such as the tibia posterior surface to remove the implant. Referring to FIGS. 5A-5C, a flexible end effector 200 which may be used with the robotic arm 106 to perform a robotic assisted hip and knee revision procedure is shown, according to an exemplary embodiment. In some embodiments, the flexible end effector 200 may be an end effector according to any of the embodiments described in U.S. patent application Ser. No. 15/436,460, which is herein incorporated by reference in its entirety.

Removing the implant manually can be difficult due to the limited access to the curtain bone area, such as a tibia posterior surface. The flexible end effector 200 is able to extend the robotic arm capability and allow access to those small areas. As shown in FIGS. 5A and 5B, the flexible end effector 200 includes two flexible bending elements 202 and 204. Each element has two degrees of freedom and can be bent less or over 90 degrees in a three-dimensional space, as shown in FIG. 5C. The end effector 200 may include a large internal channel to carry a flexible shaft. The flexible shaft is, for example, a hollow tube with a small wall thickness and is capable of spinning a cutting burr. In some embodiments, the hollow tube is capable of spinning the cutting burr at 60000 rpm. The flexible shaft's internal channel may also be used for an irrigation or suction channel. In some embodiments, the flexible elements 202 and 204 provide increased access for areas that are otherwise difficult to reach.

The end effector 200 includes a housing 206 with a base 208 and a mount 210. The base 208 secures the end effector 200 to the robotic arm 106 and provides stability to the end effector 200. Mount 210 secures a shaft 212 of the end effector 200. The shaft 212 houses a motor 214 that provides power to a cutting tool 216 located at a distal end of the end effector 200. In some embodiments, the end effector 200 also includes a suction hole 218. Suction hole 218 connects to the flexible shaft's internal channel. In some embodiments, the robotic arm 106 may be fixed and the end effector 200 may move autonomously to perform planned cuts, as described below.

A variety of cutting tools 216 could be selected for the type of bone cut to be completed. A saw could be used for a planar cut, a burr for a curved surface, a curved saw may be used to obtain access around pegs, keels and/or screws (can be cut around or cut through and removed separately, or another cutting tool could be used that is better suited for the access to the bone and the type of cut to be created. A curved tool, or a tool capable of performing a curved cut is preferred for the critical posterior portions of the knee. In an exemplary embodiment, a saw could be used to perform initial cuts, and then more specific cuts could be performed using the specialized end effector 200. In some embodiments, ultrasonic tools can be used to vibrate and break up bone cement for removal. In some embodiments, a laser can be used to melt cement. In some embodiments, a waterjet can be used to cut or break up cement.

Figure 6A:
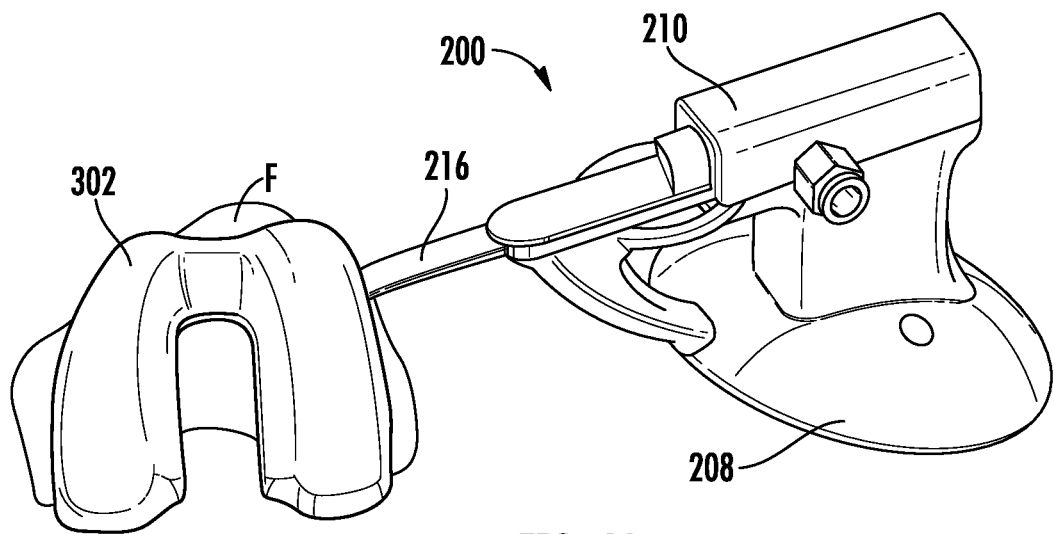
FIGS. 6A-6C illustrate various views of a femur, a femoral implant and an end effector, according to an exemplary embodiment.
Figure 6B:
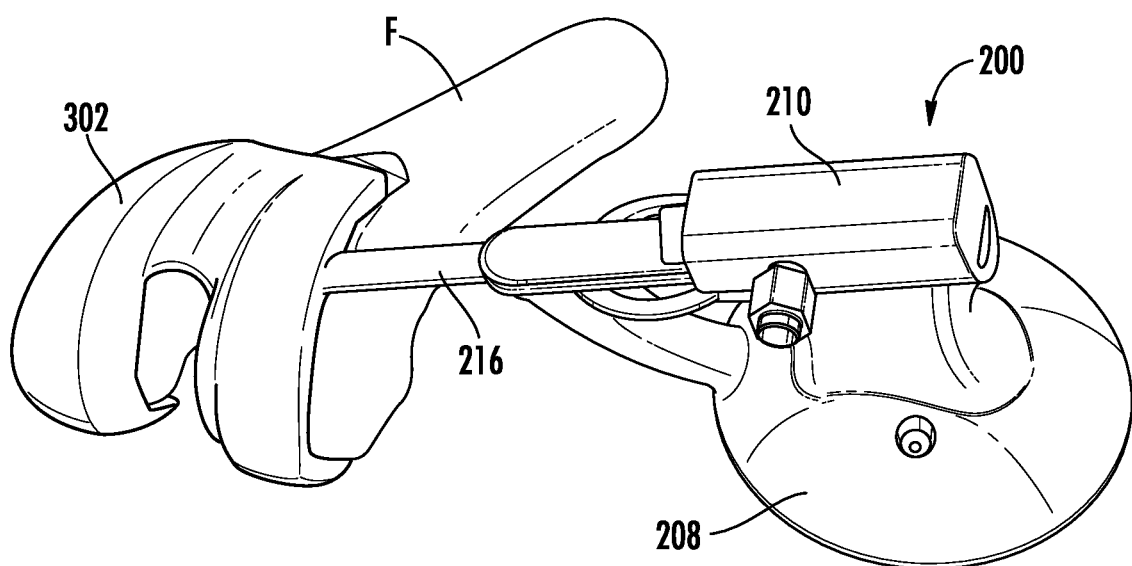
Figure 6C:
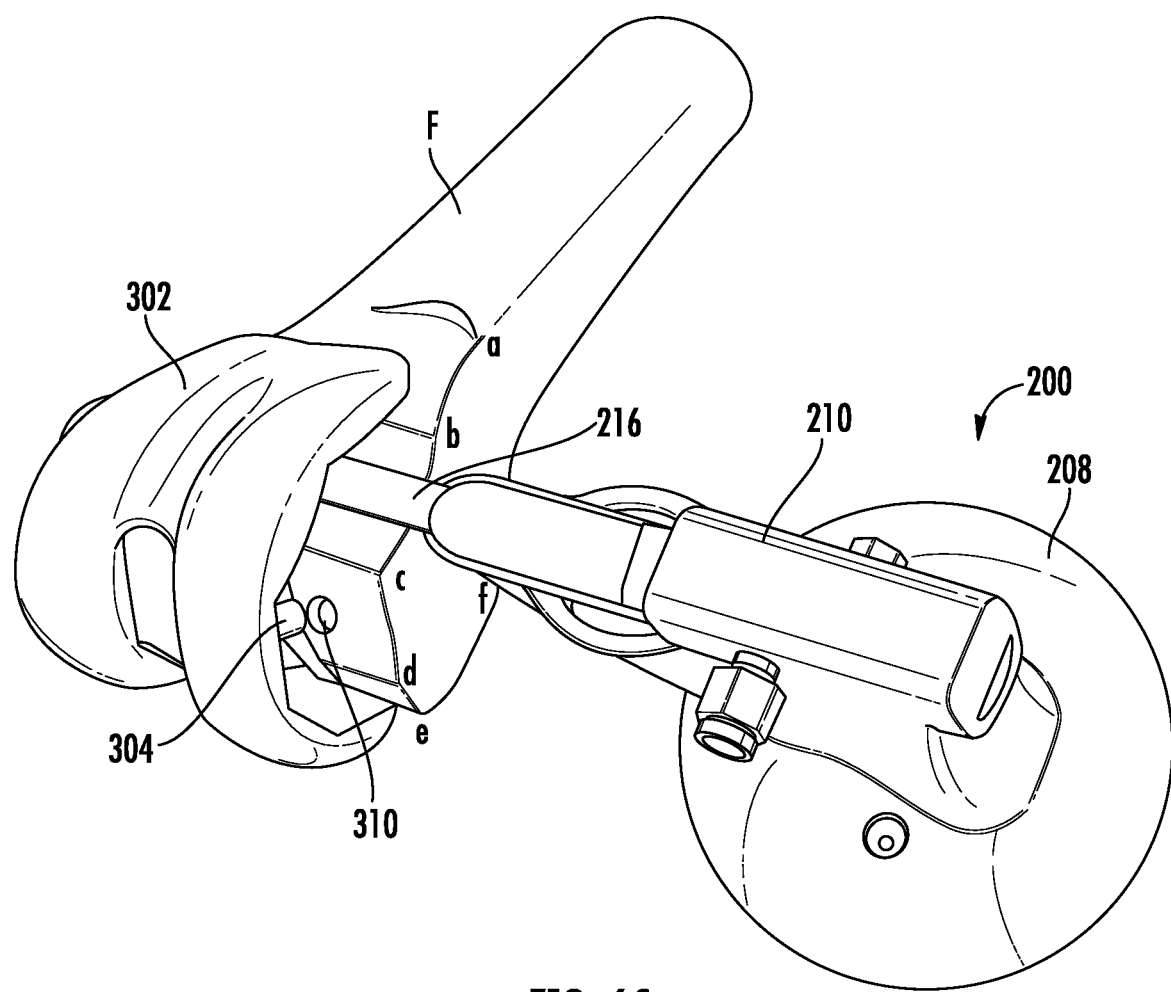

FIGS. 6A-6C illustrate various views of a femur F, a femoral implant 302 and another exemplary embodiment of an end effector 200. End effector 200 in FIGS. 6A-6C may include a base 208, a mount 210 and a cutting tool 216. The end effector 200 may be a vibratory chisel. In some embodiments, the cutting tool is capable of chipping and cutting away cement between bone and implant. The end effector 200 may be controlled and advanced by the surgeon, but may be constrained by a haptic boundary located between the bone and the implant to reduce skiving effect and ensure that all of the cement attachment would be accessed to preserve as much bone as possible. The end effector 200 may be used during the revision surgery to remove the implant by cutting along portions ab, bc, cd, de, and ef. The end effector can further by used to prepare the bone for a new implant. The bone may be prepared by creating surfaces ab, bc, cd, de, and ef in addition to a peg hole 310 for receiving peg 304 using cutting tool 216 or a variety of other cutting tools.

Figure 7A:
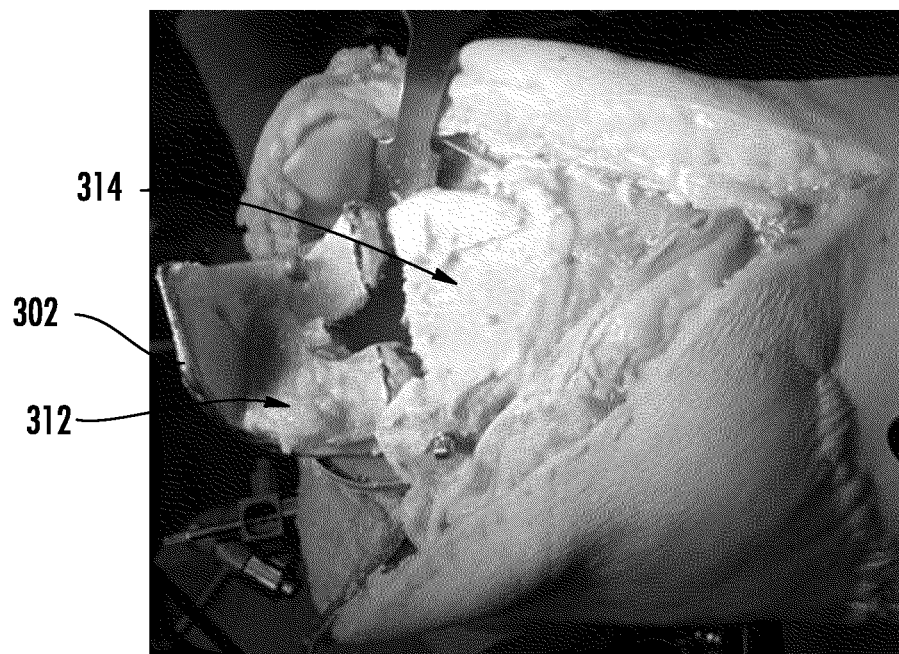
FIGS. 7A and 7B show a femoral implant and femur after non-robotic or manual removal.
Figure 7B:
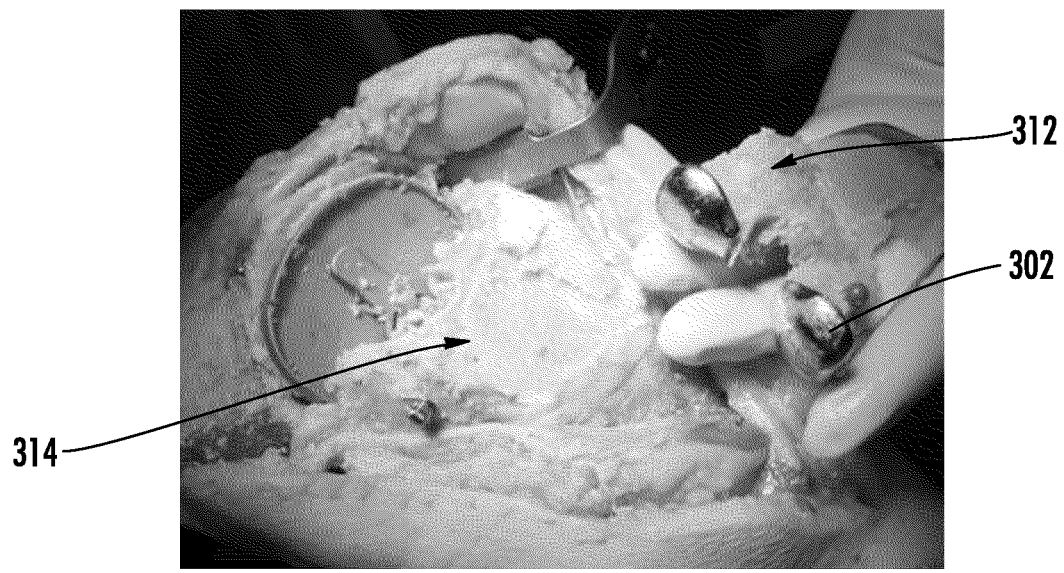

FIGS. 7A and 7B show a femoral implant 302 after removal from a femur, when the removal is performed manually or without the use of a robotic system. As can be seen in the figures, in some revision surgeries, excess bone is removed when the implant 302 is removed, shown as bone 312 remaining on the implant 302. When excess bone is removed, uneven surfaces 314 are created on the bone. Often, the excess bone removal occurs directly around a keel, peg or on the back side of the implant where it is difficult to cut the cement. In order to properly prepare the bone for a new implant, defects may need to be filled using augments, cones, or other filling methods. Video or ultrasound techniques may be used after removal of the implant to determine the characteristics of the remaining bone, to assist with correction of defects and planning re-implantation.

The surgeon may execute the revision procedure using a robotic system to aid the surgeon in removal of the primary implant using various methods, described below.

Figure 8:
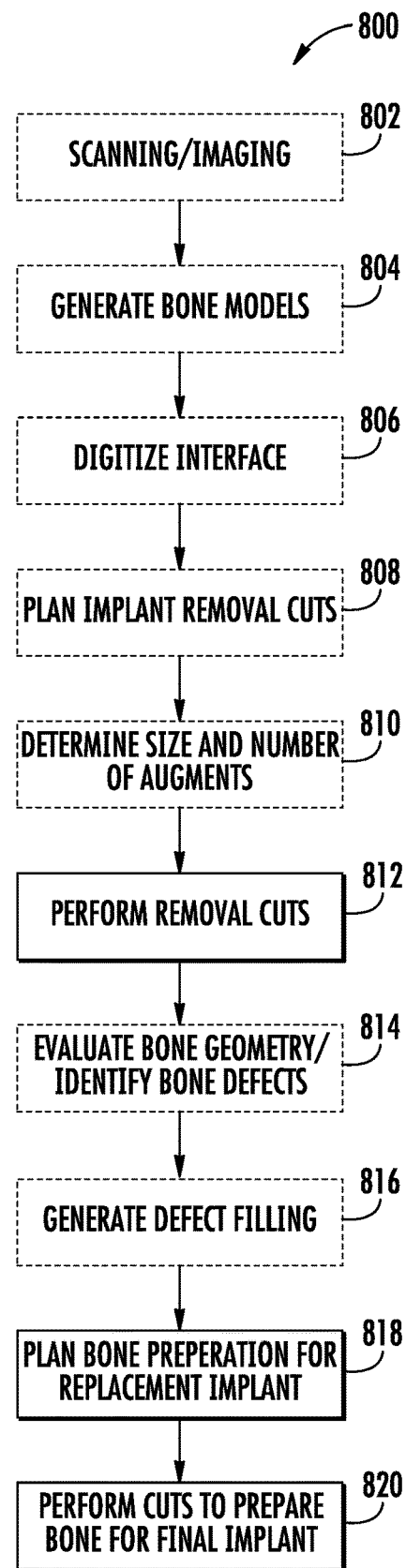
FIG. 8 is a flow chart of a method of performing a revision surgery, according to an exemplary embodiment.

FIG. 8 is a flow chart of a method 800 of performing a revision surgery, according to an exemplary embodiment. Before beginning the procedure, information related to an interface area between an implanted implant component and the bone on which it is implanted must be obtained. This can be accomplished using images of the revision site or using other tools to understand the relationship other than by images. These variations for obtaining the interface information, depicted by optional steps 802, 804, and 806 in FIG. 8, are described below.

A first exemplary embodiment of the revision surgery method utilizes images of the patient's anatomy to plan the revision. When a patient's primary case (e.g., initial surgery) is performed by a robotic-assisted system, the bone model and implant information may already be available and there is no need to recapture images to perform a revision. At the time of the revision surgery, the patient's primary knee and hip bone model and implant information are available for the robotic assisted system, as depicted in FIG. 4. In addition, models of the implant may be known and stored in a library of the surgical system for use during planning.

In other cases, patient imaging data may not be available or it is desired to obtain new images. Accordingly, initial or new scans must be performed before planning and executing the revision procedure. In such embodiments, as shown by optional step 802, the patient's anatomy is imaged using any preferred imaging modality, such as a CT or MRI scan, fluoroscopy, ultrasound, tracked markers, or by using a video camera. The images captured by the imaging device are used to create bone and implant models for use in the planning stages. (In some embodiments, in a case of a two stage revision, imaging can also be done after a spacer block is implanted. The spacer block may have features that will enable registration of the spacer block during the implantation surgery.) In some embodiments, a robotic device can be attached to an imagining device for intraoperative registration and tracking. The scan is then segmented or converted to bone models, at optional step 804. The scan may be segmented in a predefined manner, or the surgeon may be able to select segmentation parameters. In some embodiments, when using a video camera, a 3D model can be created without segmentation. In some embodiments, a 3D model can be created using imaging, a statistical model, etc. As described above, registration of the images to the physical space/anatomy is executed by the surgical system 100.

In another exemplary embodiment, where image data is not captured on the patient's anatomy or is not used, the method may capture data intraoperatively with optional step 806. In this step, the perimeter of the cement to bone or implant to bone interface is digitized using a tracked probe. Positional data of the tracked probe is captured by a tracking system, such as tracking system 101 to determine the location of the interface to be released. Digitizing the interface may also be performed in addition to models when image data, bone models, and/or implant models are available and/or used for the planning. The implant can then be registered to the primary bone model. In yet another embodiment, a camera or optical sensor may be coupled to the robotic arm to scan the implant surface and register it to the bone model. In another embodiment, a video camera can be moved around the patient to scan the bone and implant surface and create a 3D model. The surface of the implant can be probed to register the known implant location, or known features of the implant. In some embodiments, if the implant is known, probing can identify and register the implant with an implant model.

Planning the implant removal cuts is performed at step 808. In an embodiment where the image data is available from a pre-operative scan (whether it be recent scans or scans from the primary implantation surgery), the removal cuts may be based upon the images and the location of the interface between the cement and bone or the implant and bone. In some embodiments, a video camera is used to define planes and virtual boundaries. In some embodiments, a probe can be used to define planes and virtual boundaries. Alternatively, the removal cuts may be based on the intended replacement implant. In this way, the planned resection cuts may be planned to properly accommodate the new implant while also removing the current implant. In some embodiments, the planning software generates the bone preparation plan to achieve the right alignment for the patient, such as a proper alignment of the tibia and femur. According to some embodiments, the robotic system 104 helps the surgeon plan and execute the right alignment for the knee in 3D. The bone preparation plan may be carried out automatically by the planning software, or the surgeon can aid in creating the bone preparation plan. Using previous image data (x-ray, CT, MM, fluroscopic, video, etc.) and intra-operative landmarks, a visualization of ideal native anatomy can be constructed, such as joint line, etc. The system can use range of motion and soft tissue compliance as input to assist with planning the procedure, as well. In some embodiments, fiducials may be placed in the spacer block to speed registration for the re-implantation surgery. After implant removal, the robot or manual tools could be used to remove remaining cement. Hand held tracked probes or probe attachments to the robot arm could be used to identify remaining cement in a 3D model. The model can be used to create another robotic cutting path for cement removal.

In other embodiments, planning the implant removal cuts at step 808 can be based on the data collected by the digitized probe. Typically, total knee arthroscopy implant designs can include several flat bone facing surfaces. During digitization, points on each side of the implant could be collected to identify the planar surfaces. Using the perimeter data, the robotic system calculates a plan to separate the interface of interest. Using a probe to collect points to define planes that can be used for virtual boundaries. Probing the transition areas of the implant (the points between two flat surfaces can help identify the virtual boundaries). Intraoperative imaging or the use of a video camera can create models of the bone defect after implant removal. Updates to the existing model can be made by probing the defect to indicate where there is additional bone loss. This defect model can be used in the revision implant planning to assure proper implant selection to cover the defect. The defect model indicates the need for additional augment devices required to fill the defect. After the revision implants are selected, virtual boundaries are created for cutting the bone for implant insertion. Once the models and defects are created, a new plan can be generated to implement the modification and additions that need to be made to bone due to bone loss to accommodate insertion of a new implant.

As part of this planning step 808, as described above, the surgical system 100 generates a control object, such as a haptic object. The control object may define virtual boundaries that correspond to the surgeon's plan for preparing a bone. In particular, for a revision procedure, the virtual boundary is associated with a portion of the interface area that the surgeon plans to cut, remove, or otherwise alter in order to remove the current implant from the bone. A revision virtual boundary is created around the at least a portion of the interface area to allow the surgeon to precisely cut the bonding area between the bone and implant. In preferred embodiments, the virtual boundary for revision is created adjacent to the implant surface to protect from overcutting the bone. In this way, the revision boundary will minimize the bone removed, will reduce the risk of tear off the bone, and could increase the number of potential additional revision procedures which could be operated on patient in his/her lifetime. The boundary may be a planar boundary to which the cutting tool will be constrained by the virtual boundary, or a contoured boundary of any shape. The boundary may be created automatically by the system based on that image and positional data received, or may be manually created based on user input. In other embodiments, the boundary may be customizable or adjustable, for example, a surgeon may choose to move the boundary closer or further away from the interface to accommodate the quality of the bone. Using the control objects defining the virtual boundaries, the robotic system can ensure that the cutting tool does not migrate outside of a desired cutting area, the minimal bone is removed, and that the cuts are executed accurately. If the implant is known, virtual boundaries can be identified with a proposed surgical plan. The proposed surgical plan can be used as a starting template for the surgeon that can be modified to fit specific needs and/or conditions of the operation. In some embodiments, the proposed plans are generic. In some embodiments, the proposed plans provide proposed tools and/or proposed access locations for preparing the bone for implant features, such as keels, pegs, or any other structures or shapes that need to be avoided. In some embodiments, a generic template of shapes can be used in the virtual boundary planning or custom shapes can be drawn, created or selected during the surgical planning. In particular, the surgical plan may need to be customized based on the characteristics of the remaining bone after the initial implant has been removed. In some embodiments, access locations and dimensions can be identified in the proposed surgical plan. In some embodiments, entry paths can be outlined in the proposed surgical plan.

In some embodiments, the planning software can also determine the size and number of augments needed, at step 810. The planning software may select an augmentation size based on a database of information. In another embodiment, the planning software allows the user to enter the size and number of augments needed. For example, a surgeon can tell the system, via the graphical user interface, to add a 5 mm posterior augment or a medial 20 deg tibia wedge, and the planning software allows for such cuts to be executing by a surgical tool coupled to the robotic arm, instead of thru jigs. Pre-operative augment sizing and planning, made possible by using a robotic system according to the exemplary embodiments disclosed herein, save valuable operating room time and make the procedure more efficient and precise.

In step 812, the robotic system 104 tracks movement of the cutting tool, using the navigation system 101, and guides the surgeon while the planned cuts are performed. The system 104 can guide the execution of the cuts by providing a constraint on the cutting tool based on a relationship between the virtual tool (associated with the cutting tool) and the virtual boundary. The guide can be provided using haptics or the system can autonomously perform the cuts, based on the control objects generated by the system that correspond with the surgical plan. When haptics are used, the surgeon will receive feedback indicating when a haptic boundary is reached, preventing the surgeon from removing excessive bone. In some embodiments, the surgeon can use a combination of haptic control and autonomous action to perform the cuts. In some embodiments, the robotic system may also provide feedback related to the bone implant or bone cement breaking up process. For example, the robotic system may provide the surgeon with information on the progress of the cement bone or implant bone interface break. This may prevent any unintentional loss of bone while pulling out the implant if the interface is not yet properly broken.

In some embodiments, the robotic system 104 may remove hardware thru impaction. The robotic system can use the force of robot arm to "jolt" implants loose or through use of the end effector acting like a wood pecker.

Use of a robotic system allows for use of a variety of cutting tools, based on the type of bone cut to be completed. A saw could be used for a planar cut, a burr for a curved surface, a curved saw may be used to obtain access around pegs or keels, and/or access around or through screws or another cutting tool could be used that is better suited for the access to the bone and the type of cut to be created. The robotic system tracks the cutting tools and the patient to monitor the cutting procedure and provide the user with information on the progress of the cement bone or implant bone interface break. Again, this reduces unintentional loss of bone that may occur while pulling out the implant prior to properly releasing the interface. In some embodiments, a value, such as a percentage, of the surface resection can be displayed. This can give the surgeon an indication of the appropriate time to attempt implant removal. In some embodiments, if the surgeon is concerned about bone loss in a specific area, the display could show an amount of bone removal for a specific area of interest. In some embodiments, the surgeon can identify the specific area of interest to be calculated before or during surgery.

Furthermore, the robotic system or manual tools could be attached to the implant to measure an applied force for removal. Monitoring the position of the implant with respect to the bone and the force applied could give the surgeon an indication of the ease of removal. This may indicate when additional cutting is required to minimize unintentional bone loss.

After implant removal, if there are any bone defects that the planning software did not take into account, the bone defect may be digitized or identified by another means at optional step 814. At step 816, the planning software may generate the sizing information for filling the defect with various implant or biomaterial fillers. The implants and/or biomaterial fillers may be selected from a database of available implants or fillers. In some embodiments, the software can generate plans and create custom implants or fillers for filling the defect. In some embodiments, the software selects implants and/or biomaterial filler based on several factors (e.g., defect size, bone density, etc.). According to some embodiments, the robotic system 104 is able to determine the correct size of cones used to fill defects. In other embodiments, bone filler materials could be cut to the size of the defect, or the system could be configured to inject liquid fillers into the defect that could be solidified inside the patient.

In step 818, the planning software determines a desired pose of the replacement implant in the bone, and plans bone preparation for receiving the replacement implant. The planning may be carried out, and control objects created, in a similar manner as described in step 808. There are several additional ways in which the robotic system can assist with a revision procedure, in addition to executing those steps discussed above. With respect to planning and preparing for implantation of a new implant component, the display device 103 may display limb alignment/balancing screens for an assessment of how implants are installed, which will help with planning the adjustment. Furthermore, the system may help assess stem length, straight vs. bowed, cemented vs. press-fit based on bone morphology, quality, and adjacent hardware, etc. The assessment may be patient specific or predictive from a pre-defined data set. In another embodiment, the robotic system may apply distraction through a leg holder, spread, balancer, etc. to assess and define collateral tension. This can be performed at a plurality of poses, and the graphical user interface or internal algorithm can be employed to calculate joint line placement and component sizes to best restore kinematics and function. In yet another embodiment, the robotic system may be used to assist in revision surgeries from partial knee, bicompartmental, or tricompartmental into cruciate retaining, cruciate substituting, or posterior stabilized.

A video camera may also be used in step 814 to create a model of the bone after the implant has been removed. This identifies the current bone geometry without the implant, including any bone defects that require attention. The video camera and the images obtained therefrom can then be used in step 818 for planning the bone cuts, in step 820 (described below) for executing the bone cuts to prepare the bone for the replacement implant, and for placing the implant. In some embodiments, the video camera can be used during other phases of the procedure, such as for model creation, registration, or tracking the positions of the anatomy or the surgical tool(s) used during the procedure. In some embodiments, the model may also include identification of the incisions, either by selecting the edge in the system software, using color identification, image detection of retractors holding the incision open, or applying a material around the incision that can be detected by the camera. The video camera may then also be used to track the location of the incision during the procedure.

In step 820, the cuts for preparing the bone surface for placing augments, cones, fillers, and the final implant are executed. The surgeon can perform the bone preparation cuts using guidance from the system such as haptic feedback. In another embodiment, the robotic system 104 may autonomously perform the preparation cuts. As described above, the system can resect the bone for the new plan as a step to remove the existing hardware. Therefore, instead of sawing/chipping away at the existing implant, a resection is made that will help remove the implant but also be the proper cuts for the next implant.

In some embodiments, the robotic system can be used in additional ways while performing cuts to the bone. For example, the system can assist with executing adaptive cuts where subsequent cuts are made may be based on a variety of possible inputs of prior cut data or other landmarks/objectives. For example, a probe may define the distal plane and posterior tangent for example and for a defined size implant make the rest of the cuts (femur or tibia or patella). The input can be an existing resection or a target articular tangency. The computed cuts can be programmed based on inputs to create a desired outcome. In addition, the system can be used for cut refinement. A surface is probed and then skim cut, (e.g., 0.5-1 mm cut). Control boundaries, such as haptics, can be updated or generated intra-operatively as the cuts are made. In another example, the robotic system 104 can control saw performance based on bone quality. Super soft/spongy bone or hard sclerotic bone might need a "lighter" or "harder" touch in speeds and/or feeds, or even different blades.

The robotic system can also assist with placement of the implant and assessment after the implant has been replaced. For example, the display device showing a graphical user interface may be used to guide a surgeon on placement of the femoral or tibial components with stems, in terms of the offset or angled couplers or manipulating the anterior-posterior or medial-lateral position slightly to achieve less tip or cortical stress points. Furthermore, the robotic arm can be used to hold the implant in place relative to the bone while the cement is curing. In yet another embodiment, the system can help assess, via a range of motion/balancing graphical user interface, if the new construct is stable enough.

In some embodiments, the robotic system 104 may visualize implant paths or cement areas when considering other aspects of surgery, for example when a tibia tuberosity is translated and the window of tibia sectioned and moved, where the hardware is, be it trauma plates, etc. relative to knee implants, etc.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage, other magnetic storage devices, solid state storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium.

Combinations of the above are also included within the scope of machine-readable media. Machine-executable instructions include, for example, instructions and data which cause a general purpose computer, special purpose computer, or special purpose processing machines to perform a certain function or group of functions.

Although a specific order of method steps may be described, the order of the steps may differ from what is described. Also, two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish any connection steps, processing steps, comparison steps, and decision steps.

What is claimed is:

1. A method for intraoperative planning and facilitating a revision arthroplasty procedure, the method comprising:
    displaying a virtual model of a bone;
    capturing positions of a tracked probe as the tracked probe contacts points at a perimeter of a primary implant component coupled to the bone;
    generating a virtual representation of an interface between the primary implant component and the virtual model of the bone using the positions of the tracked probe;
    planning a bone resection using the virtual representation of the interface; and
    guiding execution of the bone resection.

2. The method of claim 1, wherein capturing the positions of the tracked probe as the tracked probe contacts the points at the perimeter of the primary implant component coupled to the bone comprises touching the tracked probe to edges of a plurality of flat portions of the primary implant component.

3. The method of claim 1, wherein capturing the positions of the tracked probe comprises optically detecting relative positions of a first marker of the tracked probe and a second marker attached to the bone.

4. The method of claim 1, wherein planning the bone resection using the virtual representation of the interface comprises creating a virtual boundary; and
    wherein guiding the execution of the bone resection comprises using the virtual boundary to guide removal of the primary implant component from the bone.

5. The method of claim 1, wherein planning the bone resection comprises planning a placement of a revision implant component on the bone.

6. The method of claim 5, wherein planning the placement of the revision implant component comprises calculating a joint line placement corresponding to the placement of the revision implant component.

7. The method of claim 1, further comprising registering the primary implant component with an virtual implant model based on the positions of the tracked probe.

8. The method of claim 1, wherein the virtual representation of the interface comprises a plurality of planes.

9. The method of claim 1, wherein guiding the execution of the bone resection comprises controlling a robotic device in accordance with a plan for the bone resection.

10. The method of claim 1, wherein the bone resection is configured to both remove the primary implant component from the bone and prepare the bone to receive a revision implant component.

11. The method of claim 1, further comprising planning use of an implant augment with a revision implant component.

12. The method of claim 1, further comprising:
collecting additional points on a surface exposed by the execution of the bone resection by tracking the tracked probe or using an imaging system; and
determining a bone defect based on the additional points.

13. The method of claim 12, further comprising guiding an additional bone modification based on the bone defect.

14. A system, comprising,
a display screen configured to display a virtual model of a bone;
a probe;
a tracking system configured to capture positions of the probe as the probe contacts points at a perimeter of a primary implant component coupled to the bone; and
a processing circuit configured to:
generate a virtual representation of an interface between the primary implant component and the virtual model of the bone using the positions of the probe;
enable planning of a bone resection using the virtual representation of the interface.

15. The system of claim 14, wherein the points at the perimeter of the primary implant component are positioned at edges of a plurality of flat portions of the primary implant component.

16. The system of claim 14, further comprising a robotic system comprising a cutting tool, wherein the processing circuit is configured to control the robotic system in accordance with a plan for the bone resection.

17. The system of claim 16, wherein the processing circuit is configured to:
define a virtual boundary as result of the planning of the bone resection; and
control the robotic system in accordance with the plan by causing the robotic system to constrain the cutting tool based on a relationship between a position of the cutting tool and the virtual boundary.

18. The system of claim 14, wherein the processing circuit is configured to account for cement between the primary implant component and the bone when generating the virtual representation of the interface between the primary implant component and the bone.

19. The system of claim 14, wherein the processing circuit is configured to generate the virtual representation of the interface without use of medical imaging of the primary implant component.

20. The system of claim 14, wherein the virtual representation of the interface comprises a plurality of planes.

* * * * *